United States Patent [19]

Meguro et al.

[11] Patent Number: 5,418,239

[45] Date of Patent: May 23, 1995

[54] TRICYCLIC HETEROCYCLIC COMPOUNDS, THEIR PRODUCTION AND USE

[75] Inventors: Kanji Meguro, Nishinomiya; Hiroyuki Tawada, Takatsuki; Hitoshi Ikeda, Higashiosaka, all of Japan

[73] Assignee: Takeda Chemical Industries, Ltd., Osaka, Japan

[21] Appl. No.: 117,950

[22] Filed: Sep. 8, 1993

Related U.S. Application Data

[62] Division of Ser. No. 765,182, Sep. 25, 1991, Pat. No. 5,264,454.

[30] Foreign Application Priority Data

Sep. 27, 1990 [JP] Japan .................... 2-259657
Aug. 12, 1991 [JP] Japan .................... 3-202003

[51] Int. Cl.⁶ ............ A61K 31/44; C07D 221/06; C07D 221/16
[52] U.S. Cl. ..................... 514/290; 546/79; 546/93
[58] Field of Search ............... 546/79, 93; 514/290

[56] References Cited

U.S. PATENT DOCUMENTS 3,798,226 3/1974 Meguro et al. ............ 546/159
3,862,152 1/1975 Kuwada et al. ........... 546/162

FOREIGN PATENT DOCUMENTS 0354994 2/1990 European Pat. Off. ........ 546/159

*Primary Examiner*—Alan L. Rotman
*Attorney, Agent, or Firm*—Foley & Lardner

[57] ABSTRACT

Novel heterocyclic compound of the general formula:

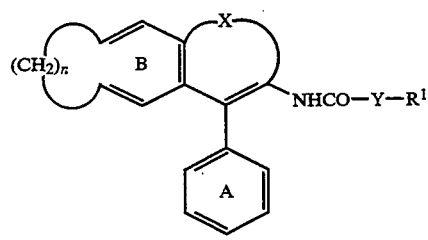

wherein ring A and ring B each means a benzene ring which is substituted or unsubstituted; X means a group of the formula:

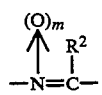

wherein $R^2$ is hydrogen an alkyl or an alkoxy; m is 0 or 1, the formula:

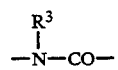

wherein $R^3$ is hydrogen or an alkyl, or the formula: —O—CO—; Y means a bond, —NH—, an $C_{1\ or\ 2}$ alkylene group or —CH=CH—; $R^1$ means a hydrocarbon group which is substituted or unsubstituted; and n means a whole number of 3 through 6, or a salt thereof, having excellent acyl-CoA:cholesterol acyltransferase inhibitory activity, and a method for preparing it and its use.

8 Claims, No Drawings

TRICYCLIC HETEROCYCLIC COMPOUNDS, THEIR PRODUCTION AND USE

This application is a divisional of Ser. No. 07/765,182, filed Sep. 25, 1991, now U.S. Pat. No. 5,264,454.

(a) Industrial Field of Utilization

The present invention relates to novel heterocyclic compounds having excellent acyl-CoA:cholesterol acyltransferase (ACAT) inhibitory activity.

(b) Prior Art

Among quinoline, 2-quinolone and coumarin derivatives substituted by nitrogen in position-3 and phenyl in position-4, compounds whose positions-6 and 7 are linked through —$(CH_2)_n$— to form a ring have not been known and, for that matter, never been a subject of research for possible exploitation as an agent for arteriosclerosis or a blood cholesterol lowering agent.

(c) Problems that the Invention is to Solve

The present invention is primarily directed to the provision of a novel heterocyclic compound or salt which has excellent acyl-CoA:cholesterol acyltransferase inhibitory activity, suppresses absorption of cholesterol from the intestinal tract and accumulation of cholesterol in the arterial wall in mammalian animals and, as such, is of value as a prophylactic and therapeutic agent for hyper-cholesterolemia, atherosclerosis and various diseases associated therewith (for example, ischemic heart diseases such as myocardial infarction etc. and cerebrovascular disorders such as cerebral infarction, cerebral apoplexy, etc.). The invention is further directed to a commercially useful process for producing said novel compound and a medicinally useful composition or pharmaceutical preparation containing said novel compound.

(d) Means for Solving the Problems

The extensive research of the inventors of the present invention into heterocyclic compounds revealed that a heterocyclic compound of the general formula:

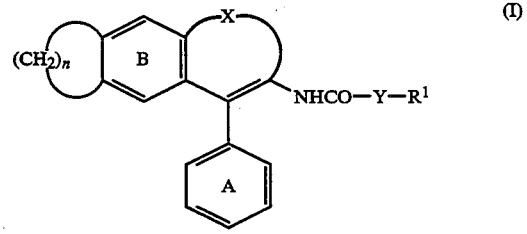

(I)

wherein ring A and ring B each mean a benzene ring which is substituted or unsubstituted, X means a group of the formula:

($R^2$ is hydrogen, alkyl or alkoxy; m is 0 or 1), the formula:

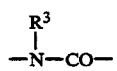

($R^3$ is hydrogen or alkyl) or the formula: —O—CO—; Y means a bond, —NH—, $C_{1\ or\ 2}$ alkylene or —CH=CH—; $R^1$ means a hydrocarbon group which is substituted or unsubstituted; and n means a whole number of 3 through 6, or a salt thereof, which is characterized in that a cycloalkyl group is condensed with ring B to form a chemically unique heterotricyclic system, has greater ACAT inhibitory activity than compounds having an uncondensed heterocycle or those having a hetero-bicyclic system owing to the above unique chemical structure and, as such, is of value as a cholesterol lowering agent and/or a therapeutic drug for arteriosclerosis. The present invention is predicated on the above findings.

The present invention, therefore, relates to:

(1) a heterocyclic compound of the formula (I) or a pharmaceutically acceptable salt thereof;

(2) A process for producing a heterocyclic compound of the general formula:

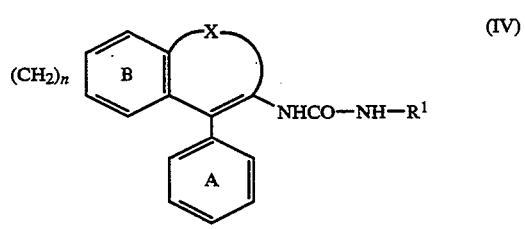

(IV)

or a salt thereof characterized by reacting a compound of the general formula:

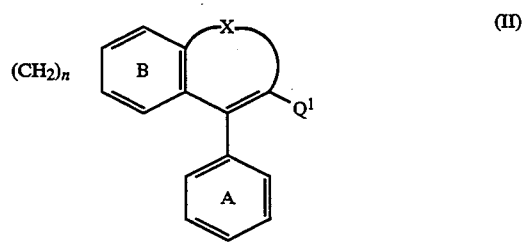

(II)

or a salt thereof with a compound of the general formula:

$$R^1\text{-}Q^2 \quad \text{(III)}$$

or a salt thereof (wherein $Q^1$ and $Q^2$ are such that either one of them is —$NH_2$ with the other being —NCO; the other symbols have the meanings defined above);

(3) A process for producing a heterocyclic compound of the general formula:

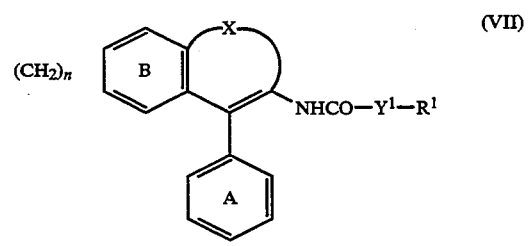

(VII)

wherein all the symbols have the meanings defined above, or a salt thereof characterized by reacting a compound of the general formula:

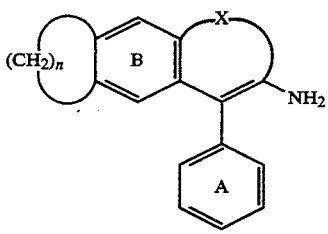

wherein all the symbols have the meanings defined above, or a salt thereof with a compound of the general formula:

$$R^1-Y^1-COOH \qquad (VI)$$

wherein $Y^1$ means a bond, an $C_{1\ or\ 2}$ alkylene group or —CH=CH—; and $R^1$ has the meaning defined above, or a reactive derivative thereof; and (4) An acyl-CoA:cholesterol acyltransferase inhibitor composition containing a heterocyclic compound of formula (I) or a salt thereof.

Referring to the above general formulas, rings A and B each mean a benzene ring which may optionally be substituted. The substituents may include, among others, halogen atoms, alkyl groups which may be halogenated, alkoxy groups which may be halogenated, alkylthio groups which may be halogenated, $C_{1-3}$ acyloxy groups (such as formyloxy, acetoxy, propionyloxy, etc.), di-alkylamino groups, and hydroxy. Examples of said halogen as substituents are fluorine, chlorine, bromine and iodine. Among the alkyl groups which may be halogenated are straight-chain or branched alkyl groups of 1 to 6 carbon atoms and the corresponding groups substituted by 1 to 5 halogen atoms such as those mentioned above, thus being exemplified by methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, 2-trifluoromethylethyl, butyl, 4,4,4-trifluorobutyl, isobutyl, sec-butyl, tertbutyl, pentyl, isopentyl, neopentyl, 5,5,5-trifluoropentyl, 4-trifluoromethylbutyl, hexyl, 6,6,6-trifluorohexyl, 5-trifluoromethylpentyl and so on. The alkoxy groups which may be halogenated or the alkylthio groups which may be halogenated may for example be the optionally halogenated groups formed upon addition of one oxygen atom or one sulfur atom to any of the aforementioned alkyl or haloalkyl groups. Thus, such optionally halogenated alkoxy groups as methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentoxy, hexyloxy, etc., and such optionally halogenated alkylthio groups as methylthio, difluoromethylthio, trifluoromethylthio, ethylthio, propylthio, isopropylthio, butylthio, 4,4,4-trifluorobutylthio, pentylthio, hexylthio, etc. can be mentioned as preferred examples. As the di-alkylamino groups, such di-$C_{1-6}$ alkylamino groups as dimethylamino, diethylamino, dipropylamino, diisopropylamino, methylethylamino, etc. can be used as preferred examples.

The substituents on rings A and B may be present in any optional position or positions of each ring and where two or more substituents are present, they may be the same or different. The number of substituents may range from 1 to 4. Preferred examples of substituted ring A are benzene rings substituted by a halogen atom, e.g. fluorine or chlorine, an $C_{1-4}$ alkyl group such as methyl or ethyl, an $C_{1-4}$ alkoxy group such as methoxy, ethoxy or the like, or an $C_{1-4}$ alkylthio group such as methylthio or the like in position-2.

Referring further to the above formulas, $R^1$ means a hydrocarbon group which may optionally be substituted. The hydrocarbon group $R^1$ includes, among others, alkyl, cycloalkyl, cycloalkyl-alkyl, aryl and aralkyl groups. The alkyl group $R^1$ is preferably a straight-chain or branched alkyl group of 1 to 8 carbon atoms, such as methyl, ethyl, propyl, isopropyl, butyl, isobutyl, sec-butyl, tert-butyl, pentyl, isopentyl, neopentyl, hexyl, heptyl, octyl and so on. The cycloalkyl group $R^1$ is preferably a $C_{3-7}$ cycloalkyl group, such as cyclopropyl, cyclopentyl, cyclohexyl and so on. The cycloalkyl-alkyl group $R^1$ is preferably a $C_{3-7}$ cycloalkyl-$C_{1-4}$alkyl group such as cyclopropylmethyl, cyclohexylmethyl, and so on. The aryl group $R^1$ is preferably an $C_{6-10}$ aryl group such as phenyl, naphthyl or the like. The aralkyl group $R^1$ is preferably an $C_{7-16}$ aralkyl group such as phenyl-$C_{1-4}$ alkyl, e.g. benzyl, 1-phenylethyl, 2-phenylethyl, 1-phenylpropyl, 2-phenylpropyl, 3-phenylpropyl, diphenylmethyl and so on. These alkyl, cycloalkyl, cycloalkyl-alkyl, aryl and aralkyl groups represented by $R^1$ may each have 1 to 5 substituents which may be the same or different. These substituents may be preferably those mentioned for rings A and B, as well as the following.

The aryl group $R^1$ is preferably phenyl and this phenyl group may have 1 to 5 substituents such as halogen, alkyl, alkoxy, di-alkylamino, hydroxy, and hydroxy acylated by $C_{1-3}$ acyl, and particularly preferably phenyl groups having 1 to 5 halogen atoms (e.g. fluorine, chlorine, bromine and iodine), particularly chlorine and/or fluorine atoms. A specific preferred example is 2,4-difluorophenyl. The preferred alkyl groups which may be attached to said phenyl group include $C_{1-4}$ alkyls such as methyl, ethyl, isopropyl, etc., and more preferably 2,6-dimethyl, 2,6-diethyl, 2-methyl-6-isopropyl and 2,6-diisopropyl. The preferred alkoxy groups which may be attached to said phenyl group are $C_{1-4}$ alkoxy groups such as methoxy, ethoxy and so on. As the di-alkylamino groups which may be attached to said phenyl group, such di-$C_{1-6}$ alkylamino groups as dimethylamino, diethylamino, dipropylamino, etc. can be used as preferred examples, and more preferred examples are 4-dimethylamino, etc. Furthermore, phenyl groups having one or more members of said $C_{1-4}$ alkyl groups or $C_{1-4}$ alkoxy groups in combination with hydroxy or hydroxy acylated by $C_{1-3}$ acyl (for example, formyl, acetyl, etc.), such as 4-acetoxy-3,5-dimethylphenyl, 4-hydroxy-3,5-dimethylphenyl, 4-acetoxy-3,5-dimethoxyphenyl, and 4-hydroxy-3,5-dimethoxyphenyl groups are preferred for $R^1$.

The aralkyl group $R^1$ is preferably benzyl, 1-phenylethyl or the like, and it is preferable that the benzene ring of such groups has 1 to 5 substituents such as halogen, alkyl, alkoxy, di-alkylamino hydroxy and-/or $C_{1-3}$ acylated hydroxy. The halogen mentioned just above is preferably fluorine or chlorine. Thus, fluorine-substituted aralkyl groups are preferred and 2,4-difluorobenzyl is most desirable. The alkyl groups which may be present as substituents on the benzene ring of benzyl, 1-phenylethyl and other groups are $C_{1-4}$ alkyls such as methyl, ethyl, isopropyl and tert-butyl, to name but a few preferred examples. The alkoxy groups which may be present on the benzene ring of benzyl, 1-phenylethyl, etc. are preferably $C_{1-4}$ alkoxy groups such as methoxy, ethoxy and so on. As the dialkylamino groups which may be present as substituents on the benzene ring, such di-$C_{1-6}$ alkylamino groups as dimethylamino, diethylamino, dipropylamino, etc. can be used as preferred examples. Particularly preferred examples of $R^1$ are benzyl groups having such $C_{1-4}$ alkoxy groups in combination with hydroxy or hydroxy acylated by $C_{1-3}$ acyl (e.g. formyl, acetyl, etc.). Thus, $R^1$ is preferably 4-acetoxy-3,5-dimethylbenzyl, 4-hydroxy-3,5-dimethylbenzyl, 4-acetoxy-3,5-dimethoxybenzyl, or 4-hydroxy-3,5-dimethoxybenzyl, for instance.

In the above formulas, X means a group of the formula:

($R^2$ is hydrogen, alkyl or alkoxy; m is equal to 0 or 1), the formula:

($R^3$ is hydrogen or alkyl) or the formula: —O—CO—. The alkyl groups represented by $R^2$ and $R^3$ include straight-chain or branched groups of 1 to 6 carbon atoms, such as methyl, ethyl, propyl, isopropyl, butyl, isobutyl, sec-butyl, tert-butyl, pentyl, isopentyl, neopentyl, hexyl and so on.

The alkoxy group $R^2$ includes, among others, straight-chain or branched alkoxy groups of 1 to 6 carbon atoms, such as methoxy, ethoxy, propoxy, isopropoxy, butoxy, isobutoxy, sec-butoxy, tert-butoxy, pentyloxy, isopentyloxy, neopentyloxy, hexyloxy and so on.

The formula:

means that, where m=1, the nitrogen atom is in the form of N-oxide.

Preferred examples of X are —N=CH—,

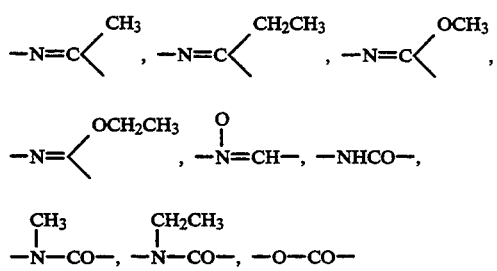

and so on.

In the above formulas, Y means a bond, —NH—, an $C_{1\ or\ 2}$ alkylene group or —CH=CH—. The $C_{1\ or\ 2}$ alkylene group may for example be —$CH_2$—, —$CH_2CH_2$— or

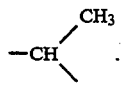

Preferred examples of Y are —NH—, —$CH_2$—, —$CH_2CH_2$— and —CH=CH—. The symbol n means a whole number of 3 to 6, preferably 3 or 4.

The heterocyclic compound of formula (I) or a salt thereof can be produced by the following and other processes.

In the first place, compound (IV), which is the compound (I) wherein Y=—NH—, can be produced by reacting compound (II) or a salt thereof with compound (III) or a salt thereof. Thus, Process (1):

A compound of the general formula:

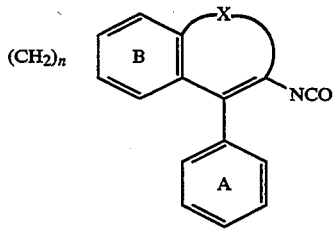 (VIII)

wherein all the symbols have the meanings defined hereinbefore, is reacted with a compound of the general formula:

 (IX)

wherein the symbol has the meaning defined hereinbefore, or a salt thereof to give compound (IV) or a salt thereof. Alternatively, Process (2):

A compound of the general formula:

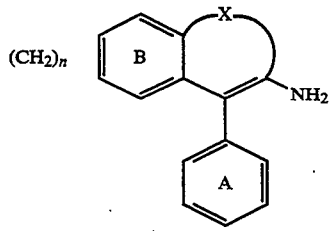 (V)

wherein all the symbols have the meanings defined hereinbefore, or a salt thereof is reacted with a compound of the general formula:

 (X)

wherein the symbol has the meaning defined hereinbefore, to give compound (IV) or a salt thereof.

Process (3):

Compound (VII), which is the compound (I) wherein Y means a bond, $C_{1\ or\ 2}$ alkylene or —CH=CH—, or a salt thereof can be produced by reacting compound (V) or a salt thereof with compound (VI) or a reactive derivative thereof.

Process (4):

Furthermore, compound (I) wherein Y=—$CH_2CH_2$— or a salt thereof can be produced by reducing compound (I) wherein Y=—CH=CH— or a salt thereof.

Each of the above processes (1) through (4) is now described in further detail.

Process (1): The reaction between compound (VIII) and compound (IX) or a salt thereof (e.g. salts with mineral acids such as hydrochloric acid, sulfuric acid, etc. or salts with organic acids such as methanesulfonic acid, benzenesulfonic acid, toluenesulfonic acid, oxalic acid, fumaric acid, maleic acid, etc.) is generally conducted in a solvent. The solvent may be any solvent that will not interfere with the reaction, such as ethers (e.g. ethyl ether, isopropyl ether, tetrahydrofuran, dioxane, dimethoxyethane, etc.), aromatic hydrocarbons (e.g. benzene, toluene, xylene, etc.), esters (e.g. methyl acetate, ethyl acetate, etc.), N,N-dimethylformamide, dimethyl sulfoxide, etc., to name but a few preferred examples. When compound (IX) is used in the form of a salt, the reaction can be advantageously conducted in the presence of an acid acceptor where necessary. The acid acceptor useful for this purpose includes tertiary amines such as trimethylamine, triethylamine, N-methylmorpholine, etc. and aromatic amines such as pyridine, picoline, N,N-dimethylaniline and so on. The proportion of such amine is 1 to 5 mole equivalents, preferably 1 to 3 mole equivalents, to each mole of a salt of compound (IX). The reaction temperature is generally —10° C. to 180° C. and preferably 0° C. to 120° C. The reaction time is generally 15 minutes to 40 hours and preferably 30 minutes to 20 hours. The proportion of (IX) or a salt thereof is 1 to 5 mole equivalents, preferably 1 to 3 mole equivalents, to each mole of (VIII).

Process (2): The reaction between compound (V) or a salt thereof (e.g. salts with mineral acids such as hydrochloric acid, sulfuric acid, etc. or salts with organic acids such as methanesulfonic acid, benzenesulfonic acid, toluenesulfonic acid, oxalic acid, fumaric acid, maleic acid, etc.) and compound (X) is carried out under the same conditions as in Process (1) described above. When (V) is used in the form of a salt, an acid acceptor similar to that mentioned for Process (1) is employed. The proportion of compound (X) is generally 1 to 5 mole equivalents and preferably 1 to 3 mole equivalents to each mole of (V).

Process (3): The reaction between compound (V) or a salt thereof (e.g. salts with mineral acids such as hydrochloric acid, sulfuric acid, etc. or salts with organic acids such as methanesulfonic acid, benzenesulfonic acid, toluenesulfonic acid, oxalic acid, fumaric acid, maleic acid, etc.) and compound (VI) is generally carried out in the presence of an appropriate condensing agent or by the procedure of converting (VI) to a reactive derivative and, then, reacting it with (V) or a salt thereof. The condensing agent mentioned above includes, among others, dicyclohexylcarbodiimide (DCC), diethyl phosphorocyanidate (DEPC), diphenylphosphoryl azide (DPPA) and so on. When such a condensing agent is employed, generally the reaction is conducted with advantage in a solvent (e.g. tetrahydrofuran, dioxane, dimethoxyethane, ethyl acetate, benzene, toluene, N,N-dimethylformamide, dimethyl sulfoxide, etc.). This reaction may be hastened by conducting it in the presence of a base and is carried out generally at—10° C. to 100° C. and preferably at about 0° C. to 60° C. The reaction time is generally 1 to 96 hours and preferably 1 to 72 hours. The proportions of (VI) and condensing agent are 1 to 5 mole equivalents each, preferably 1 to 3 mole equivalents each, to each mole of (V) or a salt thereof. The base may for example be an alkylamine such as triethylamine or a cyclic amine such as N-methylmorpholine, pyridine and so on. The proportion of the base is 1 to 5 mole equivalents, preferably 1 to mole equivalents, to each mole of compound (V) or a salt thereof. The reactive derivative of (VI) includes, among others, the corresponding acid halides (e.g. chloride, bromide, etc.), acid anhydride, mixed acid anhydride (e.g. anhydrides with methyl carbonate, ethyl carbonate, isobutyl carbonate, etc.), active esters (e.g. ester with hydroxysuccinimide, ester with 1-hydroxybenzotriazole, ester with N-hydroxy-5-norbornene-2,3-dicarboximide, ester with p-nitrophenol, ester with 8-hydroxyquinoline, etc.) and so on. Particularly preferred are acid halides. The reaction between compound (V) or a salt thereof and such a reactive derivative of (VI) is generally conducted in a solvent (e.g. chloroform, dichloromethane, ethyl ether, tetrahydrofuran, dioxane, dimethoxyethane, ethyl acetate, benzene, toluene, pyridine, N,N-dimethylformamide, etc.). This reaction may be hastened by conducting it in the presence of a base and is generally conducted at —10° C. to 120° C. and preferably at 0° C. to 100° C. The reaction time is generally 1 to 48 hours and preferably 1 to 24 hours. The proportion of the reactive derivative of (VI) is 1 to 5 mole equivalents, preferably 1 to 3 mole equivalents, to each mole of (V) or a salt thereof. The base mentioned above includes, among others, alkylamines such as triethylamine, etc., cyclic amines such as N-methylmorpholine, pyridine, etc., aromatic amines such as N,N-dimethylaniline, N,N-diethylaniline, etc., alkali metal carbonates such as sodium carbonate, potassium carbonate, etc., and alkali metal hydrogen carbonates such as sodium hydrogen carbonate, potassium hydrogen carbonate and so on. The proportion of the base is 1 to 5 mole equivalents, preferably 1 to 3 mole equivalents, to each mole of compound (V) or a salt thereof. When a water-immiscible solvent is employed, water may be added to the reaction system so as to conduct the reaction in a binary phase.

Process (4): Compound (I) wherein Y=—CH=-CH— or a salt thereof can be reduced to compound (I) wherein Y=—CH$_2$CH$_2$— or a salt thereof.

The reducing agent which can be used for this purpose includes, among others, metal hydride complexes such as lithium aluminum hydride, sodium borohydride, lithium borohydride and so on. The proportion of the reducing agent is generally 0.5 to 5 mole equivalents, preferably 0.5 to 2 mole equivalents, to each mole of compound (I) [Y=—CH=CH—] or a salt thereof. This reaction is generally conducted in a solvent (e.g. methanol, ethanol, ethyl ether, tetrahydrofuran, dioxane, etc.). The reaction temperature is generally —5° C. to 120° C. and preferably 0° C. to 100° C. The reaction time is generally 30 minutes to 12 hours and preferably 30 minutes to 6 hours.

Instead of using the reducing agent mentioned above, this reduction reaction can be carried out using a metal in combination with an acid or a metal in combination with a base or an alcohol. When the metal mentioned just above is zinc, tin or iron, for instance, an acid (e.g. hydrochloric acid, sulfuric acid, acetic acid, etc.) is chiefly used as the hydrogen source. When the metal is potassium, sodium, lithium or the like, the hydrogen source is usually a base (e.g. ammonia, methylamine, dimethylamine, ethylamine, diethylamine, etc.) or an alcohol (e.g. methanol, ethanol, propanol, etc.). The proportion of the metal for the purposes of this reaction is 1 to 10 mole equivalents, preferably 1 to 5 mole equivalents, to each mole of compound (I) [Y=—CH=-CH—] or a salt thereof. This reaction is generally conducted in a solvent (e.g. an alcohol such as methanol, ethanol, etc. or an ether such as tetrahydrofuran, dioxane, dimethoxyethane, etc.), although the acid or base used may be allowed to double as a solvent. The reaction temperature is generally 0° C. to 120° C. and preferably 0° C. to 80° C. The reaction time is generally 30 minutes to 12 hours and preferably 30 minutes to 6 hours.

This reduction reaction may also be carried out by the catalytic reduction method. The catalyst used for this purpose includes, among others, palladium black, palladium-on-carbon, platinum oxide, platinum black, Raney nickel, rhodium-on-carbon and so on. The reaction is generally conducted in a solvent (e.g. methanol, ethanol, isopropyl alcohol, tetrahydrofuran, dioxane, dimethoxyethane, formic acid, acetic acid, N,N-dimethylformamide, etc.). This reaction is conducted generally at atmospheric pressure to 20 atmospheres, preferably atmospheric pressure to 5 atmospheres. The reaction temperature is generally 0° C. to 100° C. and preferably 0° C. to 80° C. The reaction time is generally 30 minutes to 24 hours and preferably 30 minutes to 12 hours.

Where a lower alkoxy group is present on the benzene ring of the compound (I) or salt thereof thus produced by any of Processes (1) through (4) described hereinbefore, it can be converted to a hydroxy group, where necessary, by reacting the compound with boron trifluoride or the like. This reaction is generally carried out in a solvent (e.g. dichloromethane, chloroform, carbon tetrachloride, benzene, toluene, etc.) at a temperature of about —20° C. to 80° C., preferably about 0° C. to 30° C., using boron trifluoride in a proportion of about 1 to 10 mole equivalents, preferably about 1 to 5 mole equivalents, per lower alkoxy group. The reaction time is generally 15 minutes to 24 hours and preferably 30 minutes to 12 hours.

Where an acyloxy group is present on the benzene ring of the compound (I) or salt thereof thus produced by any of Processes (1) through (4) described hereinbefore, it can be converted to a hydroxy group, where necessary, by hydrolyzing the compound. This reaction is generally carried out in a solvent (e.g., methanol, ethanol, propanol, tetrahydrofuran, dioxane, dimethoxyethane, aceton, N,N-dimethylformamide, etc.) in the presence of a base (e.g., ammonia, methylamine, ethylamine, dimethylamine, potassium carbonate, sodium carbonate, potassium hydroxide, sodium hydroxide, etc.) or an acid (e.g., hydrochloric acid, hydrobromic acid, sulfuric acid, etc.). The reaction temperature is generally —10° C. to 100° C. and preferably 0° C. to 80° C. The reaction time is 10 minutes to 40 hours, preferably 15 minutes to 30 hours. The used amount of the base or acid is 1 to 200 mole equivalents, preferably 1 to 100 mole equivalents, to each mole of the starting material acyloxy derivative. This reaction may be carried out in a mixture of water and such a solvent as mentioned above.

Where a hydroxy group is present on the benzene ring of the compound (I) or salt thereof obtained by any of Processes (1) through (4) described hereinbefore, it can be converted to an alkoxy group or an acyloxy group, where necessary, by alkylating or acylating the compound as the case may be. The alkylation reaction is carried out using an alkylating agent such as optionally substituted alkane halides (e.g. chloride, bromide, iodide, etc.), sulfuric esters or sulfonic esters (e.g. methanesulfonates. p-toluenesulfonates, benzenesulfonates, etc.) in a solvent (e.g. methanol, ethanol, propanol, dimethoxyethane, dioxane, tetrahydrofuran, aceton, N,N-dimethylformamide, etc) in the presence of a base (e.g. an organic base such as trimethylamine, triethylamine, N-methylmorpholine, pyridine, picolin, N,N-dimethylaniline, an inorganic base such as potassium carbonate, sodium carbonate, potassium hydroxide, sodium hydroxide, etc.). The reaction temperature is generally —10° C. to 100° C. and preferably about 0° C. to 80° C. The proportion of such an alkylating agent is about 1 to 5 mole equivalents, preferably about 1 to 3 mole equivalents, to each mole of the staring material phenolic derivative. The reaction time is generally 15 minutes to 24 hours and preferably 30 minutes to 12 hours.

The reaction for acylating the hydroxy group on the benzene ring is carried out using a selected carboxylic acid or a reactive derivative thereof. While it depends on the kind of the acylating agent and of the starting material phenolic derivative, this reaction is generally conducted in a solvent (e.g. benzene, toluene, ethyl ether, ethyl acetate, chloroform, dichloromethane, dioxane, tetrahydrofuran, N,N-dimethylformamide, pyridine, etc.). For hastening the reaction, the reaction may be conducted in the presence of an appropriate base (e.g. sodium hydrogen carbonate, potassium hydrogen carbonate, sodium carbonate, potassium carbonate, sodium acetate, triethylamine, pyridine, etc.). The reaction derivative of such carboxylic acid includes, among others, the acid anhydride, mixed acid anhydrides, and acid halides (e.g. acid chloride, acid bromide, etc.) mentioned above. The proportion of such acylating agent is 1 to 5 mole equivalents, preferably 1 to 3 mole equivalents, to each mole of the starting material phenolic derivative. The reaction temperature is generally 0° C. to 150° C. and preferably about 10° to 100° C. The reaction time is 15 minutes to 12 hours and preferably 30 minutes to 6 hours.

When compound (I) is obtained in the free form by any of the processes described hereinbefore, it can be converted to a salt in the per se conventional manner, using a mineral acid (e.g hydrochloric acid, sulfuric acid, hydrobromic acid, etc.) or an organic acid (e.g. methanesulfonic acid, benzenesulfonic acid, toluenesulfonic acid, oxalic acid, fumaric acid, maleic acid, tartaric acid, etc.). When the product compound (I) is a salt, it can be converted to the free compound or a desired other salt in the per se conventional manner.

The resulting object compound (I) or salt thereof can be purified and isolated by the per se known separation and purification procedures (e.g. concentration, solvent extraction, column chromatography, recrystallization, etc.).

The compound (I) or pharmaceutically acceptable salt thereof has excellent acyl-CoA:cholesterol acyltransferase (ACAT) inhibitory activity and is moderate in acute and chronic toxicity. ACAT is the enzyme involved in higher fatty acid esterification of cholesterol in the cell and is known to play an important role in the absorption of cholesterol esters in the small intestine. Therefore, an inhibitor of ACAT can inhibit the absorption of dietary cholesterol from the intestinal tract and suppress increases in the blood cholesterol level as well as the accumulation of intracellular cholesterol in the arteriosclerotic focus to thereby arrest progression of atherosclerotic changes. The compound (I) or salt of the present invention which has excellent ACAT inhibitory activity is, therefore, of value as a safe prophylactic and therapeutic drug for hypercholesterolemia and atherosclerosis and various diseases associated therewith (e.g. ischemic heart diseases such as myocardial infarction and cerebrovascular disorders such as cerebral infarction and cerebral apoplexy) in mammalian animals (such as the mouse, rat, hamster, rabbit, cat, dog, horse, cattle, sheep, monkey and man).

Furthermore, among species of compound (I) and salts thereof are those compounds which inhibit production of lipid peroxides (antioxidant activity). It is known that the peroxidation of lipids in the body is associated, in a large measure, with the onset of arteriosclerosis and ischemic diseases of the brain and cardiovascular system. Therefore, the compound (I) or salt having ACAT inhibitory activity and antioxidant activity in common is particularly useful as a drug with which various associated vascular lesions can be prevented or treated from both the aspect of blood cholesterol and that of lipid peroxide.

When the compound of general formula (I) or a pharmaceutically acceptable salt thereof is used as the drug mentioned above, it can be formulated with a vehicle, excipient or diluent to provide a powder, granule, tablet, capsule, injection or the like for oral or parenteral administration. For use as an inhibitor of absorption of cholesterol, however, it is preferably administered orally. While the proper dosage depends on the kind of compound (I) or salt thereof, the route of administration chosen, and the condition and age of the patient, among other factors, the recommended dosage for oral administration to adult patients with hypercholesterolemia, for instance, is about 0.005–50 mg, preferably about 0.05–10 mg and, for still better results, about 0.2 to 4 mg/kg body weight/day, which daily dosage is preferably administered in 1–3 divided doses.

The starting compound (V) or (VIII) for the production of the compound (I) or salt according to the invention can be prepared with commercial advantage by the processes described below or any other processes analogous thereto.

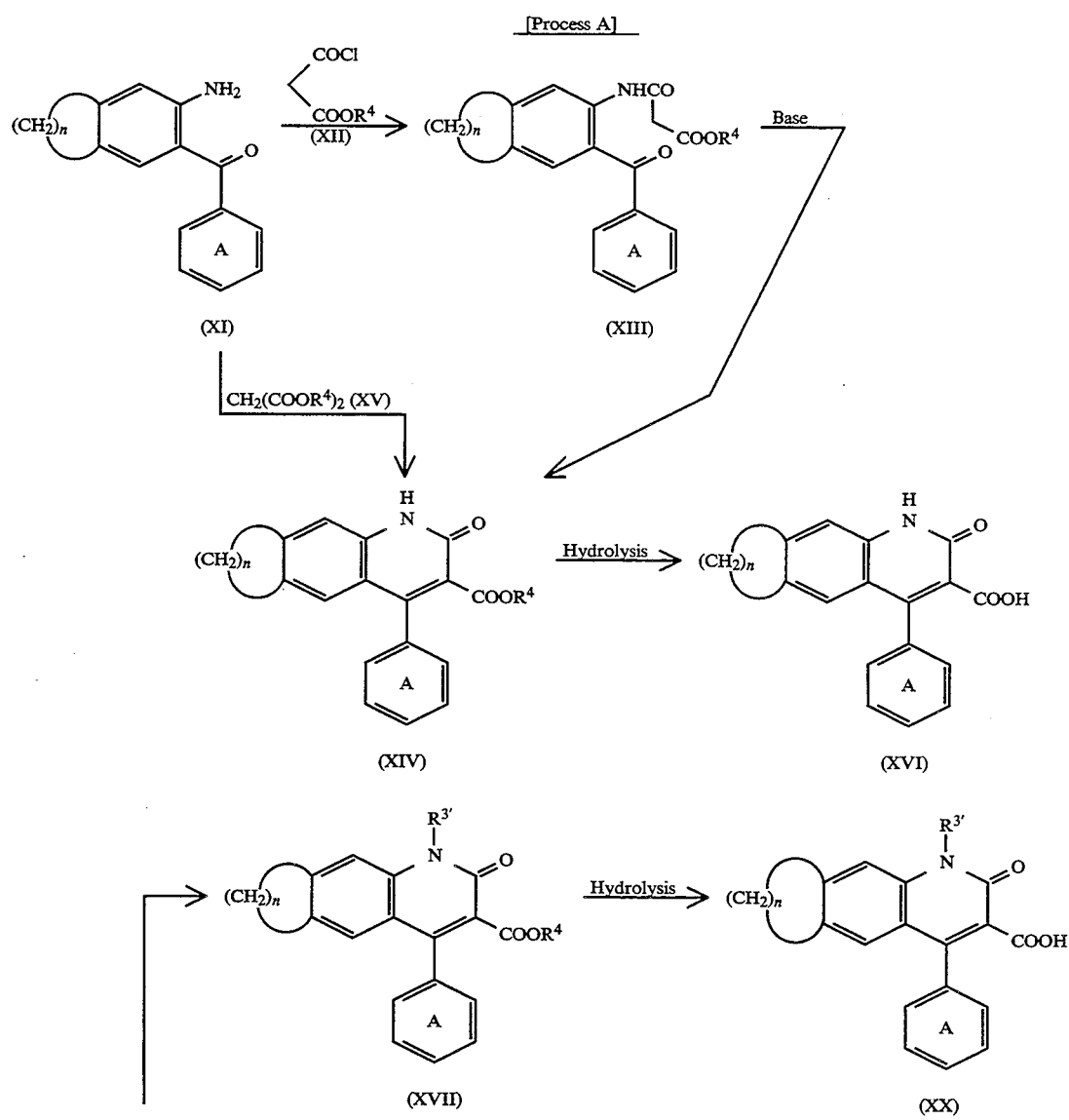

-continued
[Process A]

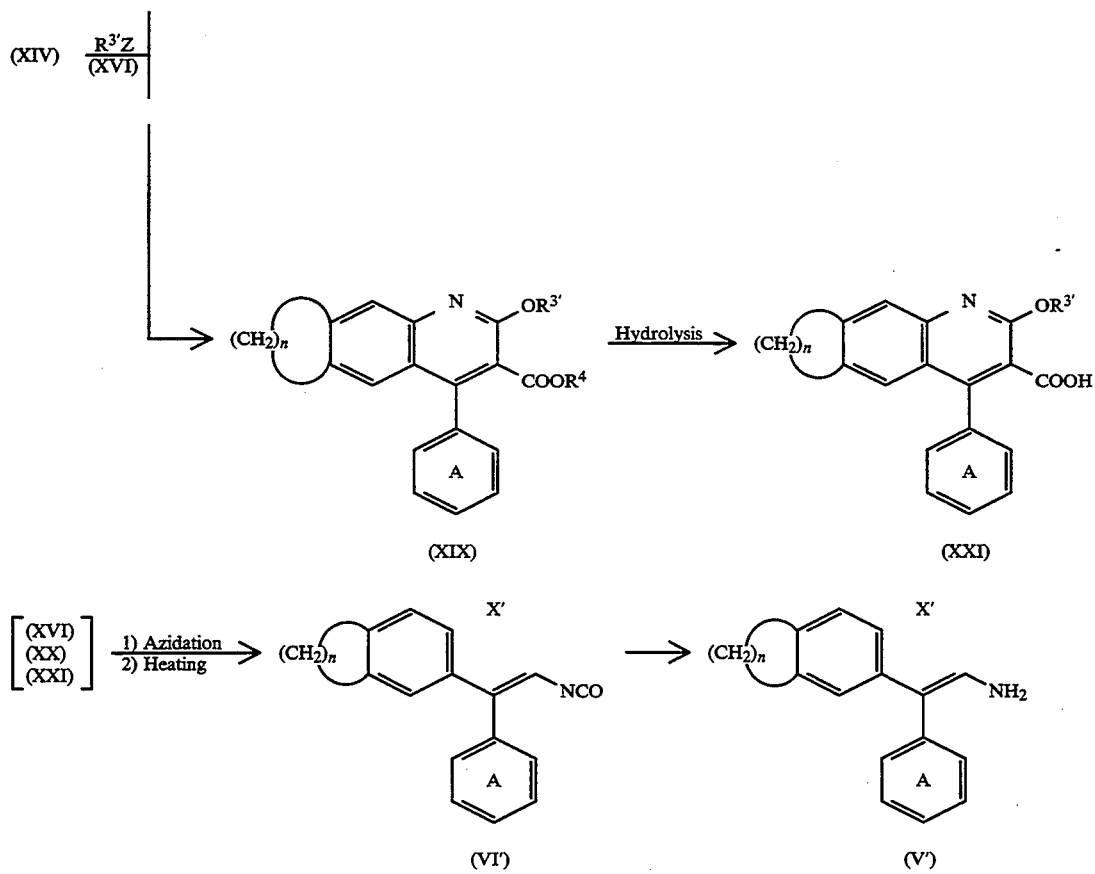

In the above formulas, $R^{3'}$ and $R^4$ each means an alkyl group; $X'$ means —NHCO—, $$-\underset{R^{3'}}{N}-CO-\quad \text{or} \quad -N=\underset{OR^{3'}}{C}-;$$

Z means a leaving group; the other symbols are as defined hereinbefore.

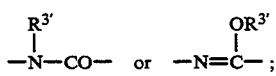

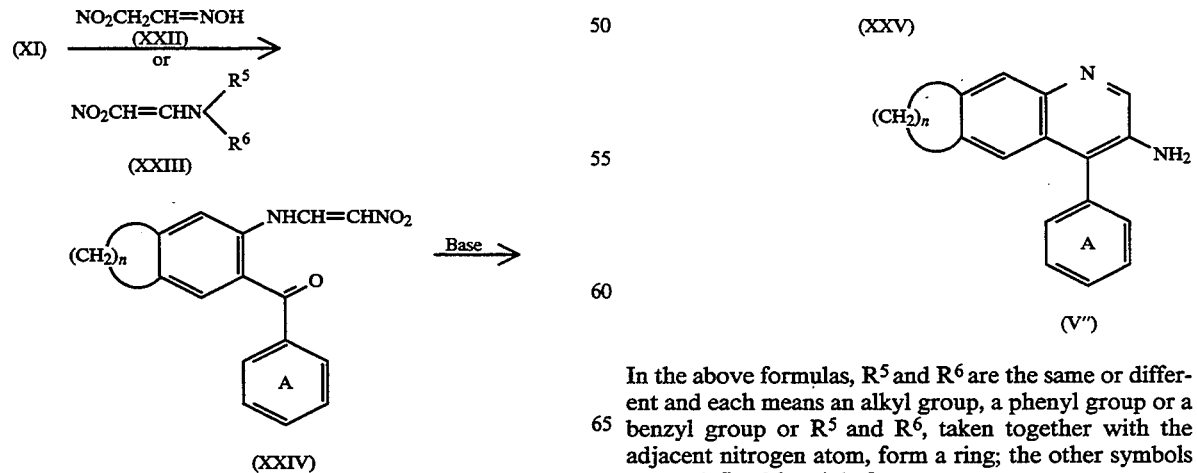

In the above formulas, $R^5$ and $R^6$ are the same or different and each means an alkyl group, a phenyl group or a benzyl group or $R^5$ and $R^6$, taken together with the adjacent nitrogen atom, form a ring; the other symbols are as defined hereinbefore.

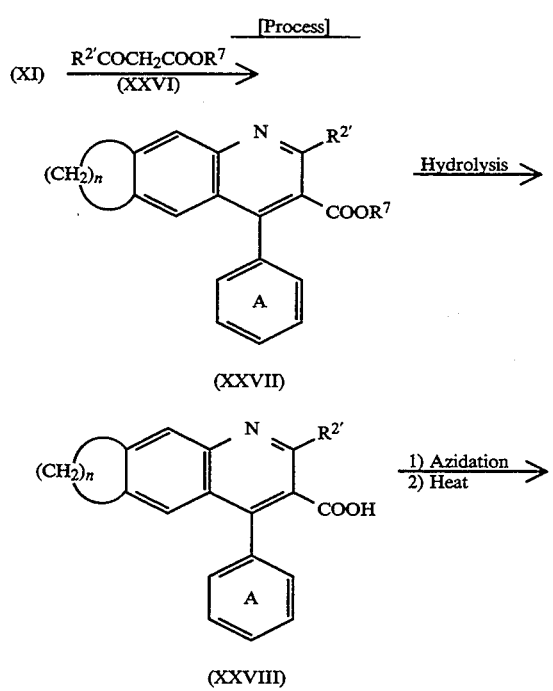
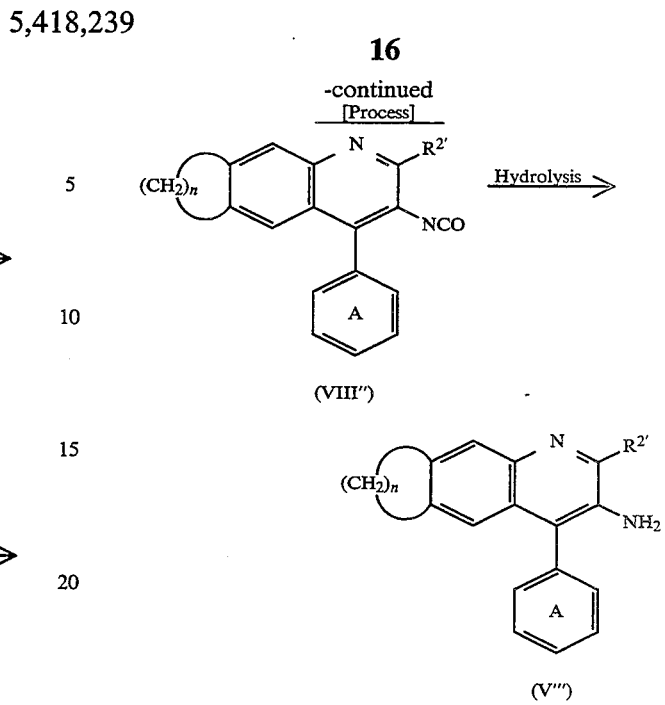
In the above formulas, $R^{2'}$ means a hydrogen atom or an alkyl group; $R^7$ means an alkyl group; the other symbols are as defined hereinbefore.
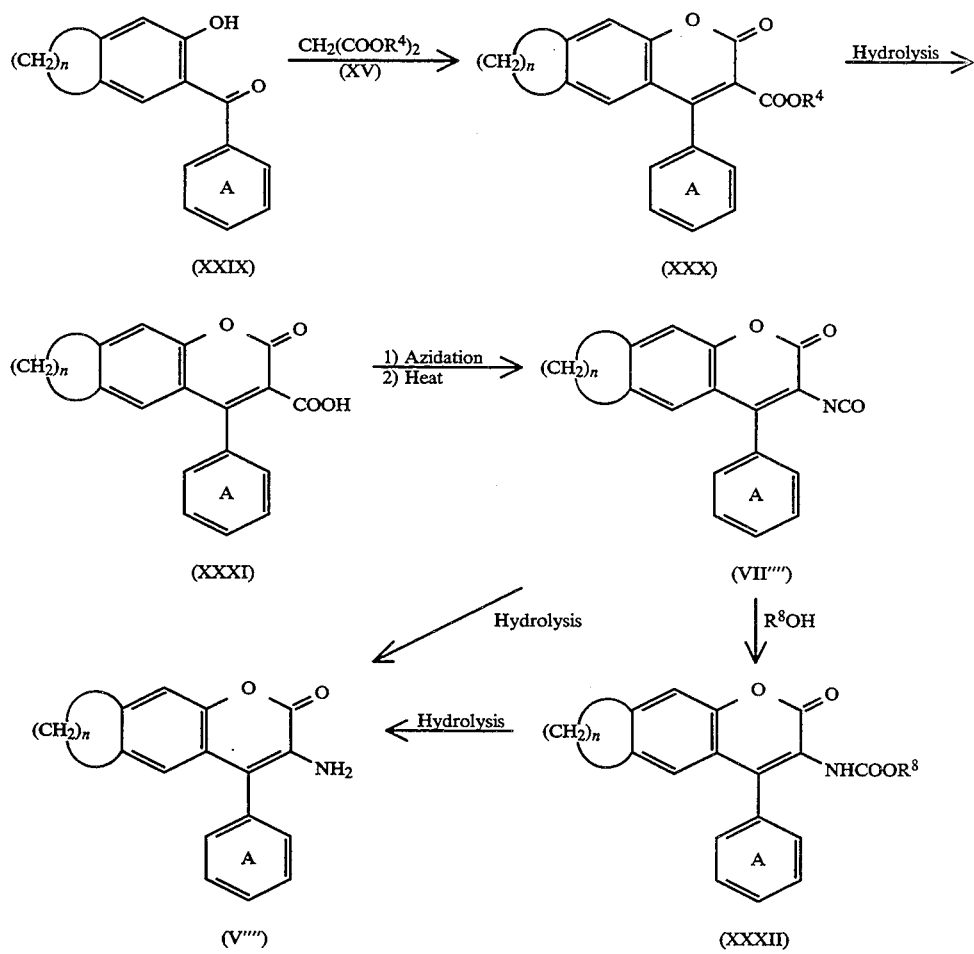

In the above formulas, $R^8$ means an alkyl group or an aralkyl group; the other symbols are as defined hereinbefore.

[Process A]

In this process, compound (XIV) can be produced by reacting an 2-aminobenzophenone derivative (XI) with a malonic diester (XV) or reacting (XI) with compound (XII), followed by cyclization with elimination of water in the presence of a base. The reaction between (XI) and (XV) to give (XIV) is generally conducted under heating in the absence of a solvent. Preferably this reaction is conducted in the presence of an amine (such as piperidine, pyrrolidine, triethylamine, 1,5-diazabicyclo[4,3,0]-non-5-ene (DBN), 1,8-diazabicyclo[5,4,0]-7-undecene (DBU), 1,4-diazabicyclo[2,2,2]octane (DABCO), etc., potassium fluoride, cesium fluoride, tetrabutylammonium fluoride or the like. The reaction temperature is generally about 60° C. to 250° C. and preferably 80° C. to 220° C. The reaction time is generally about 30 minutes to 60 hours and preferably 1 to 24 hours. The proportion of (XV) is about 1 to 5 mole equivalents, preferably 1 to 3 mole equivalents to each mole of (XI). The reaction between (XI) and (XII) is generally carried out in a solvent (e.g. ethers such as ethyl ether, tetrahydrofuran, dioxane, dimethoxyethane, etc., aromatic hydrocarbons such as benzene, toluene, xylene, etc., esters such as methyl acetate, ethyl acetate, etc., halogenated hydrocarbons such as dichloromethane, chloroform, etc., pyridine, dimethylformamide, etc.), where necessary in the presence of a base (e.g. triethylamine, pyridine, potassium carbonate, sodium carbonate, potassium hydrogen carbonate, sodium hydrogen carbonate, etc.). Where necessary, this reaction may be conducted in a solvent mixture containing water. The reaction temperature is generally about −20° C. to 150° C. and preferably about −10° C. to 120° C. The reaction time is generally about 10 minutes to 12 hours and preferably 20 minutes to 8 hours. The proportion of (XII) is about 1 to 5 mole equivalents, preferably about 1 to 3 mole equivalents to each mole of compound (XI). The product compound (XIII) is cyclized using a base to give compound (XIV). This reaction is generally conducted in a solvent (e.g. methanol, ethanol, t-butanol, benzene, toluene, xylene, tetrahydrofuran, dioxane, dimethoxyethane, dimethylformamide, etc.) in the presence of a base (e.g. potassium t-butoxide, sodium methoxide, sodium ethoxide, sodium hydride, potassium hydride, piperidine, pyrrolidine, triethylamine, DBN, DBU, DABCO, etc.). The reaction temperature is generally about 0° C. to 200° C. and preferably 20° C. to 170° C. The reaction time is generally about 30 minutes to 12 hours and preferably 1 to 8 hours. The proportion of the base is about 0.01 to 3 mole equivalents, preferably 0.05 to 2 mole equivalents, to each mole of (XIII). Where necessary, the reaction may be hastened by removing the water constantly from the reaction system with a Dean-Stark apparatus.

The reaction between compounds (XIV) and (XVII) gives rise to the N-alkyl compound (XVIII) and/or O-alkyl compound (XIX). This reaction is generally conducted in a solvent (e.g. alcohols such as methanol, ethanol, etc., ethers such as tetrahydrofuran, dioxane, dimethoxyethane, etc., ketones such as acetone, 2-butanone, etc., dimethylformamide, dimethyl sufloxide, etc.) in the presence of a base (e.g. sodium hydroxide, potassium hydroxide, sodium methoxide, sodium ethoxide, potassium t-butoxide, sodium hydride, sodium amide, potassium carbonate, sodium carbonate, triethylamine, DBU, etc.). Generally this reaction gives rise to a mixture of (XVIII) and (XIX), which can be separated by recrystallization or chromatography. Depending on the kind of (XVII) and of the solvent or the reaction temperature chosen, either of them can be selectively produced with preference. The reaction temperature is generally about −5° C. to 150° C. and preferably about 0° C. to 100° C., and the reaction time is generally about 30 minutes to 30 hours and preferably about 1 to 15 hours. The proportions of (XVII) and the base are 1 to 5 mole equivalents each, preferably 1 to 2 mole equivalents each, based on compound (XIV).

Then, (XIV), (XVIII) and (XIX) are hydrolyzed to (XVI), (XX) and (XXI), respectively. These reactions may be conducted generally in a solvent (e.g. alcohols such as methanol, ethanol, propanol, etc., ethers such as tetrahydrofuran, dioxane, diemthoxyethane, etc., or mixtures thereof), using the hydroxide of an alkali or alkaline earth metal, such as sodium hydroxide, potassium hydroxide, barium hydroxide and so on. The reaction temperature is generally about 0° C. to 120° C. and preferably about 15° C. to 100° C. The reaction time is about 15 minutes to 36 hours, preferably about 15 minutes to 20 hours. This hydrolysis reaction can be conducted under acidic conditions as well. The acid for this purpose may be a mineral acid (e.g. hydrochloric acid, sulfuric acid, phosphoric acid, hydrobromic acid, etc.) or an organic acid (e.g. formic acid, acetic acid, propionic acid, p-toluenesulfonic acid, trifluoroacetic acid, etc.). In some cases, a mixture of such acids may be employed. This reaction can be carried out using a solvent (e.g. methanol, ethanol, propanol, isopropyl alcohol, dioxane, tetrahydrofuran, methoxyethanol, dimethoxyethane, etc.). The reaction temperature is generally 20° C. to 180° C. and preferably 20° C. to 150° C. The reaction time is generally 10 minutes to 60 hours and preferably 20 minutes to 40 hours.

Then, the carboxylic acid (XVI), (XX) or (XXI) is converted to the corresponding acid azide. While many reaction techniques are described in the literature, any of them can be applied to compounds (XVI), (XX) and (XXI) in the instant process. For example, the acid azide of (XVI), (XX) or (XXI) can be synthesized by using diphenylphosphoryl azide (DPPA) as the azidating agent. This reaction can be generally conducted in a solvent inert to the reaction (e.g. ethers such as ethyl ether, isopropyl ether, dmethoxyethane, tetrahydrofuran, dioxane, etc., aromatic hydrocarbons such as benzene, toluene, xylene, etc., esters such as methyl acetate, ethyl acetate, etc., ketones such as acetone, 2-butanone, etc., pyridine, N,N-dimethylformamide, etc.). The reaction may be hastened by conducting it in the presence of a base (e.g. trimethylamine, triethylamine, N-methylmorpholine, etc.). The reaction time is generally about 5 minutes to 12 hours and preferably about 10 minutes to 6 hours. The reaction temperature is generally about −10° C. to 150° C. and preferably about −5° C. to 120° C. The proportion of DPPA is 1 to 3 mole equivalents, preferably 1 to 2 mole equivalents, to each mole of (XVI), (XX) or (XXI).

The acid azide thus obtained can be isolated and purified by the per se known procedure but is generally converted to the isocyanate (VIII′) by heating the reaction mixture as such without isolating. This transformation reaction is preferably conducted in the same solvent as used for the azidation and is generally carried out at about 20° C. to 200° C. and preferably at about 30° C. to 150° C. The reaction time is generally about 5 minutes to 10 hours and preferably about 5 minutes to 6 hours. The product compound (VIII') can be isolated by the per se known procedure but the reaction mixture may be directly used for the production of compound (I) or used as a staring material for the production of (V'). Thus, this compound (VIII') can be hydrolyzed to compound (V'). This hydrolysis reaction can be conducted under substantially the same conditions as the hydrolysis of compounds (XIV), (XVIII) and (XIX) to compounds (XVI), (XX) and (XXI).

[Process B]

The alkyl group, represented by $R^5$ and $R^6$, is preferably an alkyl group of 1 to 4 carbon atoms, such as methyl, ethyl, propyl, isopropyl and butyl. $R^5$ and $R^6$ may, taken together with the adjacent nitrogen atom, constitute a ring. Examples of such ring are 5- to 7-membered rings such as pyrrolidine, piperidine, homopiperidine and so on. These rings may have still another oxygen atom, the morpholine ring being an example.

Compound (XI) is reacted with compound (XXII) or (XXIII) to give compound (XXIV). This reaction is generally conducted in a solvent (e.g. esters such as methyl acetate, ethyl acetate, etc., ketones such as acetone, 2-butanone, etc., and aromatic hydrocarbons such as benzene, toluene, etc.) in the presence of an acid. The acid includes, among others, hydrochloric acid, hydrobromic acid, sulfuric acid, phosphoric acid, methanesulfonic acid, benzenesulfonic acid, p-toluenesulfonic acid and so on, and such acid can be used in anhydrous condition or in the form of an aqueous solution. The reaction may be conducted in a homogeneous phase or in a binary phase consisting of the solvent and water. The proportion of (XXII) or (XXIII) is about 1 to 10 mole equivalents, preferably about 1 to 5 mole equivalents, to each mole of (XI). The acid is used in a proportion of about 1 to 300 mole equivalents, preferably about 5 to 100 mole equivalents, based on (XI). The reaction temperature is generally about 0° C. to 120° C. and preferably about 10° C. to 100° C. The reaction time is about 30 minutes to 15 hours, preferably about 30 minutes to 10 hours. Then, compound (XXIV) is cyclized in the presence of a base to give (XXV). This cyclization reaction can be conducted under the same or substantially same conditions as the synthesis of (XIV) from (XIII) in Process A. Furthermore, this compound (XXV) is reduced to (V"). The reducing agent for this purpose includes lithium aluminum hydride, lithium borohydride and so on, and its proportion to (XXV) is about 0.5 to 10 mole equivalents and preferably about 1 to 5 mole equivalents. This reaction is generally carried out in a solvent (e.g. methanol, ethanol, ethyl ether, tetrahydrofuran, dioxane, dimethoxyethane, etc.). The reaction temperature is generally about $-5°$ C. to 120° C. and preferably about 0° C. to 100° C. The reaction time is generally about 15 minutes to 12 hours and preferably 30 minutes to 8 hours.

Instead of using the above reducing agent, this reduction reaction can also be conducted using a metal in combination with an acid, a metal salt in combination with an acid, or a metal in combination with a base. The metal mentioned above includes, among others, zinc, tin and iron, while the metal salt may for example be tin(II) chloride. Here, the hydrogen source is an acid (e.g. hydrochloric acid, sulfuric acid, hydrobromic acid, acetic acid, etc.). When potassium, sodium, lithium or the like is used as said metal, the hydrogen source is generally a base (e.g. ammonia, methylamine, dimethylamine, ethylamine, diethylamine, etc.), although an alcohol (e.g. methanol, ethanol, propanol, etc.) can also be employed. The proportion of said metal or metal salt to (XXV) in this reaction is about 1 to 20 mole equivalents, preferably about 1 to 10 mole equivalents. The reaction is generally conducted in a solvent (e.g. alcohols such as methanol, ethanol, etc. and ethers such as tetrahydrofuran, dioxane, dimethoxyethane, etc.), although the acid or base as the hydrogen source may double as the solvent. The reaction temperature is generally about 0° C. to 150° C. and preferably about 10° C. to 120° C. The reaction time is generally about 15 minutes to 12 hours and preferably about 30 minutes to 10 hours.

The reduction reaction can also be conducted by the catalytic reduction method. The catalyst used for this purpose includes, among others, palladium black, palladium-on-carbon, platinum oxide, platinum black, Raney nickel, rhodium-on-carbon and so on. This reaction is generally conducted in a sovlent (e.g. methanol, ethanol, isopropyl alcohol, tetrahydrofuran, dioxane, dimethoxyethane, formic acid, acetic acid, N,N-dimethylformamide, etc.). The reaction temperature is about 0° C. to 120° C, preferably about 10° C. to 100° C. The reaction pressure is generally atmospheric pressure to 50 atmospheres and preferably atmospheric pressure to 10 atmospheres.

[Process C]

The alkyl group $R^7$ is preferably an alkyl group of 1 to 4 carbon atoms, such as methyl, ethyl, propyl, isopropyl and butyl.

Compound (XI) is reacted with compound (XXVI) to give (XXVII). This reaction is generally conducted in a solvent (e.g. alcohols such as methanol, ethanol, propanol, etc., ethers such as tetrahydrofuran, dioxane, dimethoxyethane, etc., aromatic hydrocarbons such as benzene, toluene, xylene, etc., and organic acids such as formic acid, acetic acid, propionic acid, etc.) but may be conducted in the absence of a solvent in the presence of an acid catalyst (e.g. hydrochloric acid, sulfuric acid, hydrobromic acid, methanesulfonic acid, benzenesulfonic acid, p-toluenesulfonic acid, etc.). The proportion of (XXVI) to (XI) is about 1 to 10 mole equivalents, preferably about 1 to 5 mole equivalents. The proportion of the said catalyst to (XI) is about 0.01 to 2 mole equivalents, preferably about 0.05 to 1 mole equivalent. The reaction temperature is generally about 0° C. to 200° C. and preferably about 10° C. to 150° C. The reaction time is generally about 15 minutes to 24 hours and preferably about 30 minutes to 15 hours. The product compound (XXVII) is then converted to (XXVIII)→(VIII")→(V"'). The procedures and conditions of these reactions may be similar to those described for Process A.

[Process D]

The alkyl group $R^8$ is preferably an alkyl group of 1 to 4 carbon atoms, such as methyl, ethyl, propyl, isopropyl, butyl, isobutyl and tert-butyl. The aralkyl group $R^8$ is preferably benzyl.

Compound (XXIX) is reacted with compound (XV) to give (XXX). This reaction is conducted in a solvent (e.g. alcohols such as methanol, ethanol, propanol, etc., ethers such as tetrahydrofuran, dioxane, dimethoxyethane, etc., aromatic hydrocarbons such as benzene, toluene, xylene, etc., dimethylformamide, dimethyl sulfoxide, etc.) in the presence of a base (e.g. pyrrolidine, piperidine, DBN, DBU, DABCO, sodium hydride, potassium tert-butoxide, sodium methoxide, etc.). In certain instances, the reaction can be conducted in the presence of a base without employing a solvent to give (XXX). The reaction temperature is generally 20° C. to 250° C. and preferably 50° C. to 220° C. The reaction time is generally 30 minutes to 50 hours and preferably 1 to 24 hours. The proportion of (XV) to (XXIX) is 1 to 10 mole equivalents, preferably 1 to 5 mole equivalents. The proportion of the base to (XXIX) is 0.01 to 3 mole equivalents, preferably 0.05 to 2 mole equivalents. The product (XXX) can be converted to (XXXI) and further to (VIII'''') and (V''''). The procedures and conditions of such reactions may be those mentioned for Process A.

The compound (VIII'''') can be reacted with an alcohol (e.g. methanol, ethanol, propanol, tert-butanol, benzyl alcohol or the like) to give compound (XXXII). This reaction is generally conducted using the corresponding alcohol as a solvent, but a solvent system consisting of said alcohol and a solvent such as ethers (e.g. tetrahydrofuran, dioxane, dimethoxyethane, etc.), aromatic hydrocarbons (e.g. benzene, toluene, xylene, etc.), N,N-dimethylformamide, pyridine, etc., may also be employed in certain instances. The reaction temperature is generally about 0° C. to 150° C. and preferably about 10° C. to 120° C. The reaction time is 5 minutes to 12 hours, preferably 15 minutes to 10 hours. The compound (XXXII) is hydrolyzed to (V''''). This reaction can be conducted substantially under the same conditions as those of the hydrolysis reaction described for Process A.

The compound (XXXII) wherein $R^8$ is a benzyl group is subjected to hydrogenolysis to yield (V'''). This reaction can be conducted by the same catalytic reduction method as the preparation of (V'') from (XXV) or an analogous one thereto.

The starting compounds (XI) and (XXIX) can be produced by the following processes, for instance, or any processes analogous thereto.

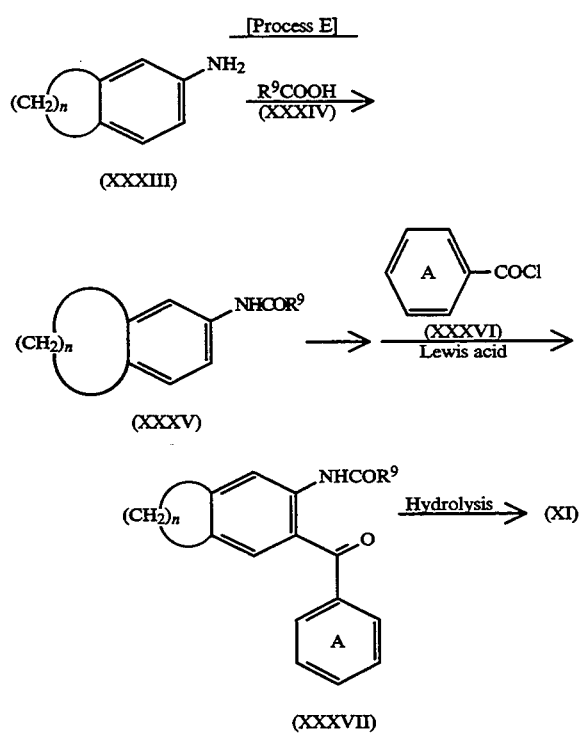

(XXXIII)

(XXXV)

(XXXVII)

In the above formulas, $R^9$ means an alkyl group or an aryl group; the the symbols have the meanings defiend hereinbefore.

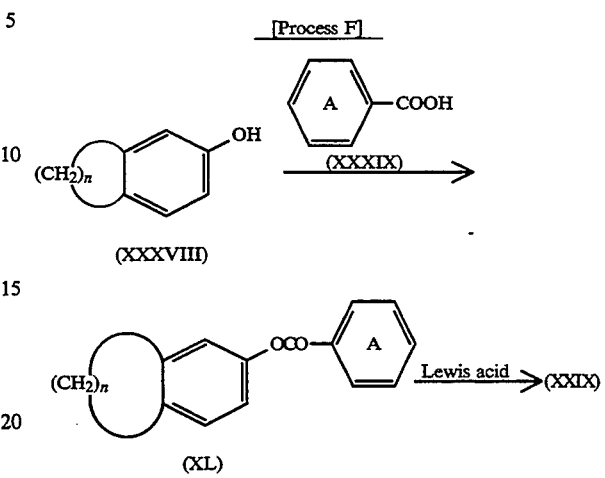

(XXXVIII)

(XL)

In the above formulas, the symbols are as defiend hereinbefore.

Processes E and F are described in detail below.

[Process E]

The alkyl group $R^9$ is preferably an alkyl group of 1 to 4 carbon atoms, such as methyl, ethyl, propyl, isopropyl and butyl. The aryl group $R^9$ is preferably phenyl, which may have substituents similar to those mentioned for ring A. The reaction between (XXXIII) and (XXXIV) to give (XXXV) is generally conducted in the presence of an appropriate condensing agent (e.g. DCC, DEPC, DPPA, etc.) or alternatively using a reactive derivative (e.g. acid chloride, acid bromide, acid anhydride, mixed acid anhydride, active ester, etc.) of (XXXIV). Of the above reactive drivatives, the acid chloride and acid anhydride are particularly preferred. The reaction conditions may be similar to those used in the production of (VII) from (V) and (VI). The (XXXV) is then reacted with (XXXVI) to produce (XXXVII) in the presence of a Lewis acid (e.g. iron (III) chloride, zinc chloride, aluminum chloride, tin tetrachloride, boron trifluoride, etc.) in a solvent inert to the reaction (e.g. dichloromethane, 1,2-dichloroethane, nitroethane, nitrobenzene, dichlorobenzene, etc.). Where necessary, the reaction may be carried out by mixing (XXXV) and (XXXVI) with a Lewis acid in the absence of a solvent. The reaction temperature is generally 0° C. to 220° C. and preferably 50° C. to 180° C. The reaction time is generally 20 minutes to 20 hours and preferably 30 minutes to 10 hours. The proportions of (XXXVI) and Lewis acid to each mole of (XXXV) are 1 to 7 mole equivalents each, preferably 1 to 3 mole equivalents each. Then, compound (XXXVII) is hydrolyzed to compound (XI). This hydrolysis reaction is preferably conducted under acidic conditions, using a mineral acid such as sulfuric acid, hydrochloric acid, hydrobromic acid or the like. This reaction can be carried out using a mineral acid as the solvent or, where necessary, acetic acid, ethylene glycol or the like may be added to the reaction system for dissolving compound (XXXVII). The reaction temperature is generally about 50° C. to 200° C. and preferably 70° C. to 180° C. The proportion of the mineral acid to (XXXVI) is 5 to 500 mole equivalents, preferably 10 to 300 mole equivalents.

[Process F]

First, compound (XL) is synthesized from compound (XXXVIII) and compound (XXXIX) or a reactive derivative thereof. This reaction can be carried out by the same procedure as, or a procedure analogous to, the procedure described for the production of (XXXV) from (XXXIII) and (XXXIV) in Process E. Then, compound (XXXIX) is produced from compound (XL). This reaction is conducted in a solvent (e.g. dichloromethane, 1,2-dichloroethane, nitroethane, nitrobenzene, dichlorobenzene, etc.) in the presence of a Lewis acid (e.g. iron (III) chloride, zinc chloride, aluminum chloride, tin tetrachloride, boron trifluoride, etc.). Where necessary, however, (XL) may be reacted with a Lewis acid in the absence of a solvent. The reaction temperature is generally about 20° C. to 200° C. and preferably about 50° C. to 180° C. The reaction time is generally 5 minutes to 8 hours and preferably 10 minutes to 6 hours. The proportion of the Lewis acid to (XL) is 1 to 10 mole equivalents, preferably 1 to 5 mole equivalents.

The product compounds (XI) and (XXIX) can be isolated and purified by the per se known procedures but the respective reaction mixtures as such may be used as starting materials in the next stages.

(e) Action

While the compound (I) and salt of the invention have excellent ACAT inhibitory activity, pertinent pharmacologic test data are presented below.

(1) Acyl-CoA:cholesterol transferase (ACAT) inhibitory activity

[Method]

Samples of ACAT enzyme were prepared from the small intestinal mucosal microsome fraction of a 6-week-old male sprague-Dawley rat fasted for 20 hours in accordance with the procedure described by Heider et al, Journal of Lipid Research 24, 1127 (1982).

ACAT activity was determined in accordance with the method of Helgerud et al., Journal of Lipid Research 22, 271 (1981), by measuring the amount of labeled cholesterol ester produced from [1-$^{14}$C]oloyl-CoA and endogenous cholesterol.

[Results]

Table 1 shows the labeled cholesterol ester production inhibiting rate (%) at $10^{-6}$ M of the test compound as an indicator of ACAT inhibitory activity. The 50% inhibitory concentration (IC$_{50}$) determined by plotting at a plurality of concentration levels is also shown.

TABLE 1

| Test compound (Example No.) | ACAT inhibition rate (%) | IC$_{50}$(M) |
| --- | --- | --- |
| 1 | 99.3 | $3.8 \times 10^{-9}$ |
| 2 | 99.2 | $3.9 \times 10^{-9}$ |
| 3 | 99.5 | — |
| 4 | 91.5 | — |
| 8 | 99.0 | — |
| 9 | 94.6 | — |
| 10 | 98.7 | — |
| 11 | 75.6 | — |
| 12 | 91.1 | — |
| 13 | 89.9 | — |
| 15 | 89.6 | — |
| 16 | 94.4 | — |
| 17 | 97.6 | — |
| 18 | 86.9 | — |
| 19 | 98.2 | — |

Table 1 shows clearly that (I) or a salt thereof has very high ACAT inhibitory activity.

(2) Plasma cholesterol lowering activity in cholesterol-fed rats

[Method]

Male Sprague-Dawley rats aged 7 weeks were divided into groups based on body weight and put on a 1% cholesterol diet (the rat diet supplemented with 0.5% cholic acid and 5% olive oil) containing 0.0003% of the test compound for 7 days. The blood was sampled from surfeited rats between 8:30 and 10:00 a.m. and the plasma cholesterol concentration was enzymatically determined. The amount of the compound ingested was calculated from the food consumption.

[Results]

TABLE 2

| Test compound Example No. | Dose (mg/kg/day) | Plasma cholesterol mg/dl |
| --- | --- | --- |
| Control group | 0 | 181.8 ± 60.4 |
| 1 | 0.242 ± 0.012 | 80.8 ± 18.6* |
| 2 | 0.227 ± 0.012 | 78.5 ± 10.2* |
| 3 | 0.234 ± 0.014 | 78.1 ± 12.6* |

Each value is mean ± S.D.
*p < 0.05 (t-test, against control group)

It will be apparent from Table 2 that the test compounds significantly lowered the plasma cholesterol level under cholesterol loading. Table 2 indicates, also, that compound (I) or a salt thereof has excellent plasma cholesterol lowering activity.

(f) Examples

The following reference and working examples are further illustrative of the present invention and should by no means be construed as defining the metes and bounds of the invention.

The elution procedure in column chromatography in the reference and working examples was performed under TLC (thin layer chromatography) monitoring. The TLC monitoring was performed using Merck's Silica Gel 60 F$_{254}$ for the TLC plate, the column chromatographic eluent for the developer solvent, and a UV detector for detection of spots. As the column packing silica gel, the same Silica Gel 60 (70–230 mesh) from Merck & Co. was used.

The symbols used in the working and reference examples have the following meanings:

mg: milligram, g: gram, ml: milliliter, m.p.: melting point.

EXAMPLE 1

To a solution of 3-amino-4-(2-chlorophenyl)-7,8-dihydro-6H-cyclopenta[g]quinoline (2.5 g) in tetrahydrofuran (25 ml) was added 2,4-difluorophenyl isocyanate (1.2 ml) dropwise and the mixture was stirred for 5 hours at room temperature. The solvent was then distilled off to give crystals of N-[4-(2-chlorophenyl)-7,8-dihydro-6H-cyclopenta[g]quinolin-3-yl]-N'-(2,4-difluorophenyl)urea. The crystals were collected by filtration and washed with isopropyl ether (3.42 g, 89.8%). Recrystallization from acetic acid-water gave colorless needles, m.p. 247°–248° C.

Elemental analysis, for C$_{25}$H$_{18}$ClF$_2$N$_3$O Calcd.: C, 66.74; }t, 4.03; N, 9.34 Found : C, 66.85; H, 3.97; N, 9.26

EXAMPLE 2

N-[7,8-Dihydro-4-(2-methylphenyl)-6H-cyclopenta[g]-quinolin-3-yl]-N'-(2,4-difluorophenyl)urea was synthesized in the same manner as Example 1. Yield 86.5%, m.p. 252°–254° C. (recrystallized from acetic acid-water)

Elemental analysis, for $C_{26}H_{21}F_2N_3O$ Calcd.: C, 72.71; H, 4.93; N, 9.78 Found: C, 72.61; H, 5.00; N, 9.67

EXAMPLE 3

Triethylamine (1.2 ml) was added dropwise to a mixture of 4-(2-methylphenyl)-2-oxo-2,6,7,8-tetrahydrocyclopenta[g][1]benzopyran-3-carboxylic acid (2.56 g), DPPA (2.64 g) and benzene (32 ml). The mixture was stirred at room temperature for 30 minutes and, then, on reflux for 30 minutes. Then, 2,4-difluoroaniline (1.0 ml) was added and the mixture was further refluxed for 30 minutes. The reaction mixture was washed with water, 1N HCl and water in the order mentioned and, then, dried ($MgSO_4$). The solvent was then distilled off to give N-(2,4-difluorophenyl)-N'-[4-(2-methylphenyl)-2-oxo-2,6,7,8-tetrahydrocyclopenta[g][1]-benzopyran-3-yl]urea as oil. The oil was crystallized by addition of isopropyl ether (3.4 g, 95.2%). Recrystallization from acetone gave colorless prisms, m.p. 223°–224° C.

Elemental analysis, for $F_{26}H_{20}F_2N_2O_3$ Calcd.: C, 69.95; H, 4.52; N, 6.27 Found : C, 70.11; H, 4.51; N, 6.20

EXAMPLE 4

To a mixture of 2,4-difluorophenylacetic acid (206 mg), DMF (1 drop) and tetrahydrofuran (4 ml) was added oxalyl chloride (0.13 ml) dropwise. The resulting mixture was stirred at room temperature for 1 hour and the solvent was then distilled off to give 2,4-difluorophenylacetyl chloride. This chloride was dissolved in dichloromethane (5 ml) followed by addition of 3-amino-4-(2-chlorophenyl)-7,8-dihydro-6H-cyclopenta[g]quinoline (294 mg) and N,N-dimethylaniline (0.13 ml). The mixture was further stirred at room temperature for 3 hours, after which it was washed with water, saturated aqueous solution of $NaHCO_3$ and water in the order mentioned and dried (over $MgSO_4$). The solvent was then distilled off to give 4-(2-chlorophenyl)-3-(2,4-difluorophenylacetylamino)-7,8-dihydro-6H-cyclopenta(g)quinoline as oil. This oil was crystallized from isopropyl ether (yield 342 mg, 76.3%). Recrystallization from ethanol gave colorless prisms, mp. 179°–180° C.

Elemental analysis, for $C_{26}H_{19}ClF_2N_2O$ Calcd.: C, 69.57; H, 4.27; N, 6.24 Found : C, 69.57; H, 4.56; N, 6.31

EXAMPLE 5

By the procedure of Example 4, there was synthesized 3-(4-acetoxy-3,5-dimethoxycinnamoylamino) -4-(2-chlorophenyl)-7,8-dihydro-6H-cyclopenta[g]quinoline. Yield 44.0%, m.p. 155°–157° C. (as recrystallized from ethanol)

Elemental analysis, for $C_{31}H_{27}ClN_2O_5 \cdot C_2H_5OH$ Calcd.: C, 67.28; H, 5.65; N, 4.76 Found : C, 67.01; H, 5.99; N, 4.62

EXAMPLE 6

By the procedure of Example 3, there was synthesized N-(4-acetoxy-3,5-dimethylphenyl)-N'-[4-(2-methylphenyl)-2-oxo-2,6,7,8-tetrahydrocyclopenta-[g][1]benzopyran-3-yl]urea. Yield 82.8%, m.p. 248°–249° C. (recrystallized from acetone)

Elemental analysis, for $C_{30}H_{28}N_2O_5$ Found: C, 72.56; H, 5.68; N, 5.64 Calcd.: C, 72.61; H, 5.63; N, 5.67

EXAMPLE 7

By the procedure of Example 3, there was synthesized N-(4-acetoxy-3,5-dimethoxyphenyl)-N'-[4-(2-methylphenyl)-2-oxo-2,6,7,8-tetrahydrocyclopenta -[g][1]benzopyran-3-yl]urea. Yield 77.7%, m.p. 233°–234° C. (as recrystallized from ethanol-dichloromethane)

Elemental analysis, for $C_{30}H_{28}N_2O_7$ Found: 68.17; H, 5.43; N, 5.30 Calcd.: 68.00; H, 5.29; N, 5.07

EXAMPLE 8

By the procedure of Example 3, there was synthesized N-[4-(3,5-di-tert-butyl-4-hydroxyphenyl)-2-oxo-2,6,7,8-tetrahydrocyclopenta[g] [1]benzopyran-3-yl]-N'-(2,4-difluorophenyl]urea. Yield 54.5%, m.p. 240°–243° C. (as recrystallized from acetone)

Elemental analysis, for $C_{33}H_{34}F_2N_2O_4 \cdot \frac{1}{2}H_2O$ Calcd.: C, 69.58; H, 6.19; N, 4.92 Found: C, 69.28; H, 6.14; N, 4.73

EXAMPLE 9

By the procedure of Example 3, there was synthesized N-(4-dimethylaminophenyl)-N'-[4-(2-methyl phenyl)-2-oxo-2,6,7,8-tetrahydrocyclopenta[g] [1] benzo -pyran-3-yl]urea. Yield 73.3%, m.p. 154°–156° C. (as recrystallized from acetone)

Elemental analysis, for $C_{28}H_{27}N_3O_3$ Calcd.: C, 74.15; It, 6.00; N, 9.26 Found : C, 74.10; II, 6.10; N, 9.17

EXAMPLE 10

By the procedure of Example 3, there was synthesized N-(2,4-difluorophenyl)-N'-[4-(2-methyl phenyl)-6,7,8,9-tetrahydro-2-oxo-2H-naphtho[2,3-b]pyran-3-yl]urea. Yield 96.1%, m.p. 222°–223° C. (as recrystallized from acetone)

Elemental analysis, for $C_{27}H_{22}F_2N_2O_3$ Calcd.: C, 70.43; H, 4.82; N, 6.08 Found : C, 70.75; H, 4.90; N, 6.03

EXAMPLE 11

By the procedure of Example 3, there was synthesized N-(4-acetoxy-3,5-dimethylphenyl)-N'-[4-(2-chlorophenyl)-7,8-dihydro-2-methoxy-6H-cyclopenta[g]-quinolin-3-yl]urea. Yield 68.5%, m.p. 247°–248° C. (as recrystallized from acetone-hexane)

Elemental analysis, for $C_{30}H_{28}ClN_3O_4$ Calcd.: C, 67.98; H, 5.32; N, 7.93 Found : C, 67.80; H, 5.30; N, 7.91

EXAMPLE 12

By the procedure of Example 3, there was synthesized N-(4-acetoxy-3,5-dimethylphenyl)-N'-[1-methyl-4-(2-methylphenyl)-2-oxo-1,2,7,8-tetrahydro-6H-cyclopenta[g]quinolin-3-yl]urea. Yield 80.6%, m.p. 178°–180° C. (as recrystallized from acetone-hexane)

Elemental analysis, for $C_{31}H_{31}N_3O_4$ Calcd.: C, 73.06; H, 6.13; N, 8.25 Found : C, 72.81; H, 6.33; N, 7.95

EXAMPLE 13

To a mixture of 3,4-dimethoxycinnamic acid (540 mg), DMF (2 drops) and tetrahydrofuran (10 ml) was added oxalyl chloride (0.27 ml) dropwise. The mixture was stirred at room temperature for 40 minutes, at the end of which time the solvent was distilled off to give 3,4-dimethoxycinnamoyl chloride. The chloride was dissolved in dichloromethane (10 ml) followed by addition of 3-amino-4-(2-methylphenyl)-7,8-dihydrocyclopenta [g] [1]benzopyran-2(6H)-one (582 mg) and N,N-dimethylaniline (0.25 ml). The mixture was then stirred at room temperature for 20 hours, after which it was washed with water, dried ($MgSO_4$) and distilled to remove the solvent. The residue was chromatographed on silica gel and eluted with benzene-acetone (9:1) to give 3-(3,4-dimethoxycinnamoylamino) -4-(2-methylphenyl)-7,8-dihydrocyclopenta[g] 1benzopyran-2(6H)-one as oil. The oil was crystallized from ethanol-isopropyl ether (648 mg, 67.4%). Recrystallization from acetone gave colorless needles, m.p. 159°–160° C.

Elemental analysis, for $C_{30}H_{26}NO_5$ Calcd.: C, 74.98; H, 5.45; N, 2.91 Found: C, 74.58; H, 5.89; N, 2.63

EXAMPLE 14

By the procedure of Example 13, there was synthesized 3-(3,5-di-tert-butyl-4-hydroxycinnamoylamino)-4-(2-methylphenyl)-7,8-dihydrocyclopenta[g] [1]-benzopyran-2(6H)-one as powder. Yield 25.0%

Elemental analysis, for $C_{36}H_{39}NO_4$ Calcd.: C, 78.66; H, 7.15; N, 2.55 Found : C, 78.90; H, 7.01; N, 2.21

EXAMPLE 15

By the procedure of Example 13, there was synthesized 3-(3,5-di-tert-butyl-4-hydroxyphenylacetylamino)-4-(2-methylphenyl)-7,8-dihydrocyclopenta -[g] [1]benzopyran-2(6H)-one. Yield 69.8%, m.p. 189°–190° C. (as recrystallized from ethanol-hexane)

Elemental analysis, for $C_{35}H_{39}NO_4$ Calcd.: C, 78.18; H, 7.31; N, 2.60 Found : C, 77.99; H, 7.07; N, 2.68

EXAMPLE 16

To a solution of N-(4-acetoxy-3,5-dimethoxyphenyl)-N'-[4-(2-methylphenyl)-2-oxo-2,6,7,8-tetrahydrocyclopenta[g] [1]benzopyran-3-yl]urea (400 mg) in tetrahydrofuran (4 ml) was added 10% methanolic hydrochloride (4 ml). The mixture was stirred at room temperature for 8 hours and the solvent was then distilled off. The residue was diluted with water and extracted with ethyl acetate. The extract was washed with water, dried (MgSO$_4$) and distilled to remove the solvent. To the residue was added ethanol to give crystals of N-(4-hydroxy-3,5-dimethoxyphenyl)-N'-[4-(2-methylphenyl)-2-oxo-2,6,7,8-tetrahydrocyclopenta [g] [1]benzopyran-3-yl]urea (330 mg, 66.7%). Recrystallization from ethanol gave colorless needles, m.p. 176°–179° C.

Elemental analysis, for $C_{28}H_{26}N_2O_6 \cdot \frac{1}{2}H_2O$ Calcd.: C, 67.87; H, 5.49; N, 5.65 Found: C, 68.16; H, 5.43; N, 5.33

EXAMPLE 17

By the procedure of Example 16, there was synthesized N-(4-hydroxy-3,5-dimethylphenyl)-N'-[4-(2-methylphenyl)-2-oxo-2,6,7,8-tetrahydrocyclopenta -[g] [1]benzopyran-3-yl]urea. Yield 78.7%, m.p. 238°–239° C.

Elemental analysis, for $C_{28}H_{26}N_2O_4$ Calcd.: C, 73.99; H, 5.77; N, 6.16 Found: C, 74.01; H, 5.81; N, 5.93

EXAMPLE 18

To a solution of 3-(3,4-dimethoxycinnamoylamino)-4-(2-methylphenyl)-7,8-dihydrocylopenta [g] [1]benzopyran-2(6H)-one (400 mg) in dichloromethane (6 ml) was added boron tribromidedichloromethane (1:2, 1 ml) dropwise with ice-cooling and stirring. The mixture was further stirred under ice-cooling for 1 hour and, then, added gradually to ethanol (5 ml) with ice-cooling. The mixture was diluted with water and extracted with ethyl acetate, the extract was washed with water and dried (MgSO$_4$), and the solvent was distilled off to give crystals of 3-(3,4-dihydroxycinnamoylamino)-4-(2-methylphenyl)-7,8-dihydrocyclopenta [g] [1]benzopyran-2(6H)-one (361 mg, 95.8%). Recrystallization from ethanol gave light brown prisms, m.p. 295°–297° C.

Elemental analysis, for $C_{28}H_{23}NO_5$ Calcd.: C, 74.16; H, 5.11; N, 3.09 Found : C, 73.95; It, 5.07; N, 2.97

EXAMPLE 19

By the procedure of Example 3, there was synthesized N-(2,4-difluorophenyl)-N'-[1-methyl-4-(2-methylphenyl)-2-oxo-1,2,7,8-tetrahydro-6H-cyclopenta-[g]quinolin-3-yl]urea. Yield 78.9%, m.p. 230°–232° C. (as recrystallized from methanol-chloroform)

Elemental analysis, for $C_{27}H_{23}F_2N_3O_2$ Calcd.: C, 70.58; H, 5.05; N, 9.14 Found : C, 70.60; H, 5.02; N, 9.04

REFERENCE EXAMPLE 1

1) 2-Chlorobenzoyl chloride (11.8 g) was added dropwise to a stirred mixture of 5-aminoindan (9.0 g), potassium carbonate (9.3 g), ethyl acetate (90 ml) and water (90 ml) under ice-cooling. The mixture was further stirred under ice-cooling for one hour, at the end of which time the organic layer was separated, washed with water, dried (MgSO$_4$) and distilled to remove the solvent. The procedure gave crystals of 5-2-chlorobenzoylamino)indan. The crystals were collected by filtration and recrystallized from isopropyl ether to give colorless needles, m.p. 144°–145° C.

2) A mixture of 5-(2-chlorobenzoylamino)indan (16 g), 2-chlorobenzoyl chloride (15.5 g) and tin tetrachloride (10.2 ml) was heated at 130° C. for 30 minutes and, then, diluted with ethyl acetate (150 ml), followed by addition of 3N HCl (150 ml). The organic layer was separated and washed with water, 2N NaOH and water in the order mentioned and the solvent was distilled off. The residue was chromatographed on silica gel and eluted with hexane-acetone (4:1) to give 6-(2-chlorobenzoyl)-5-(2-chlorobenzoylamino)indan as oil (16.0 g, 66.2%).

3) A mixture of 6-(2-chlorobenzoyl)-5-(2-chlorobenzoylamino)indan (16.0 g) and 70% H$_2$SO$_4$ (100 ml) was heated at 120° C. for 30 minutes and, then, poured in ice-water (300 ml). The solution was alkalinized with concentrated aqueous ammonia and extracted with ethyl acetate. The extract was washed with water and dried (MgSO$_4$) and the solvent was distilled off to give 5-amino-6-(2-chlorobenzoyl)indan as yellow oil (10.0 g, 94.3%). Recrystallization from hexane gave yellow prisms, m.p. 90°–92°.

4) 1-Morpholino-2-nitroethene (3.93 g) was added to a mixture of 5-amino-6-(2-chlorobenzoyl)indan (4.50 g), 6N HCl (15 ml) and acetone (45 ml) and the whole mixture was stirred at room temperature for one hour. To this reaction mixture was added water to give crystals of 6-(2-chlorobenzoyl)-5-(2-nitroethenylamino)indan (5.40 g, 95.2%). Recrystallization from ethanol gave yellow needles, mp. 225°–226° C.

Elemental analysis, for $C_{18}H_{15}ClN_2O_3$ Calcd.: C, 63.07; H, 4.41; N, 8.17 Found: C, 62.74; H, 4.56; N, 7.80

5) 6-(2-Chlorobenzoyl)-5-(2-nitroethenylamino)indan (4.8 g) was added in small portions to a solution of DBU (4.8 g) in benzene (50 ml) with heating at 90° C. The mixture was refluxed for 30 minutes and, then, washed with 2N HCl and water and dried (MgSO$_4$). The solvent was then distilled off to give crystals of 4-2-chlorophenyl)-7,8-dihydro-3-nitro-6H -cyclopenta[g]quinoline. The crystals were collected by filtration and washed with methanol (4.50 g, 99.1%). Recrystallization from ethanol gave light brown prisms, mp. 175°–176° C.

Elemental analysis, for $C_{18}H_{13}ClN_2O_2$ Calcd.: C, 66.57; H, 4.03; N, 8.63 Found : C, 66.29; H, 4.17; N, 8.33

6) To a mixture of 4-(2-chlorophenyl)-7,8-dihydro-3-nitro-6H-cyclopenta[g]quinoline (4.50 g), dioxane (45 ml) and concentrated hydrochloric acid (15 ml) was added tin(II) chloride dihydrate (9.5 g) followed by stirring at room temperature for one hour. The reaction mixture was then diluted with water, made strongly alkaline with 6N NaOH and extracted with chloroform. The extract was washed with water and dried (MgSO$_4$) and the solvent was distilled off to give crystals of 3-amino-4-(2-chlorophenyl)-7,8-dihydro-6H -cyclopenta[g]quinoline. The crystals were collected by filtration and washed with isopropyl ether (3.45 g, 83.3%). Recrystallization from ether gave colorless needles, mp 179°–180° C.

Elemental analysis, for $C_{18}H_{15}ClN_2$ Calcd.: C, 73.34; H, 5.13; N, 9.50 Found: C, 73.30; H, 5.32; , 9.20

REFERENCE EXAMPLE 2

The following compounds were synthesized in the same manner as Reference Example 1.

1) 5-(2-Methylbenzoylamino)indan: mp 160°–161° C.
2) 6-(2-Methylbenzoyl)-5-(2-methylbenzoylamino)indan: mp 124°–125° C.
3) 5-Amino-6-(2-methylbenzoyl)indan: mp 97°–98° C.
4) 6-(2-Methylbenzoyl)-5-(2-nitroethenylamino)indan: mp 205°–206° C.
5) 4-(2-Methylphenyl)-7,8-dihydro-3-nitro-6H-cyclo-penta[g]quinoline: mp 151°–152° C.
6) 3-Amino-4-(2-methylphenyl)-7,8-dihydro-6H-cyclo-penta(g)quinoline: mp 165°–166° C.

REFERENCE EXAMPLE 3

1) To an ice-cooled mixture of 5-hydroxyindan (13.4 g), triethylamine (14.0 ml) and dichloromethane (150 ml) was added 2-methylbenzoyl chloride (15.4 ml) dropwise with constant stirring. The mixture was further stirred under ice-cooling for one hour, after which it was washed with water and dried (MgSO$_4$). The solvent was then distilled off to give 5-(2-methylbenzoyloxy)indan as oil in quantitative yield.

2) A mixture of 5-(2-methylbenzoyloxy)indan, obtained in 1) above, and aluminum chloride (16 g) was heated at 120° C. for 30 minutes. After cooling, the reaction mixture was added to a mixture of HCl (100 ml) and ethyl acetate (100 ml) for extraction into ethyl acetate. The extract was washed with water and dried (MgSO$_4$) and the solvent was distilled off to give 5-hydroxy-6-(2-methylbenzoyl)indan as oil (24.6 g, 97.6%). Recrystallization from ethanol gave colorless prisms, mp 61°–62° C.

3) A mixture of 5-hydroxy-6-(2-methylbenzoyl)indan (10.08 g), diethyl malonate (12.8 g) and DBU (0.6 ml) was heated at 180° C. for 6 hours. After cooling, the reaction mixture was chromatographed on silica gel and eluted with hexane-ethyl acetate (5:1). The solvent was then distilled off to recover ethyl 4-(2-methylphenyl)-2-oxo-2,6,7,8-tetrahydrocyclopenta[g][−1]benzopyran-3-carboxylate as oil, which was then crystallized from ethanol (7.08 g, 50.9%). Recrystallization from ethanol gave colorless prisms, mp 113°–114° C.

Elemental analysis, for $C_{22}H_{20}O_4$ Calcd.: C, 75.84; H, 5.79 Found: C, 75.70; H, 5.91

4) A mixture of ethyl 4-(2-methylphenyl)-2-oxo-2,6,7,8-tetrahydrocyclopenta[g][1]benzopyran-3-carboxylate (5.0 g), concentrated hydrochloric acid (13 ml) and acetic acid (25 ml) was refluxed for 12 hours. To this reaction mixture was added water, whereupon 4-(2-methylphenyl)-2-oxo-2,6,7,8-tetrahydrocyclopenta[g][1]benzopyran-3-carboxylic acid was obtained as crystals (4.5 g, 97.8%). Recrystallization from acetone-hexane gave colorless prisms, mp 213°–214° C.

Elemental analysis, for $C_2H_{16}O_4$ Calcd.: C, 74. 99; H, 5.03 Found : C, 74. 85; H, 5.24

5) To a solution of 4-( 2-methylphenyl)-2-oxo-2,6,7,8tetrahydrocyclopenta [g][1]benzopyran-3-carboxylic acid (2.5 g) and diphenyl phosphoryl azide (DPPA, 2.58 g) in tert-butanol (25 ml) was added triethylamine (1.1 ml) dropwise and the mixture was stirred at room temperature for 30 minutes and, then, refluxed for 4 hours. The solvent was distilled off and the residue was diluted with water and extracted with ethyl acetate. The extract was washed with water, dried (MgSO$_4$) and distilled to remove the solvent, whereby 3-tert-butyloxycarbonylamino-4-(2-methylphenyl)-7,8-dihydro-6H-cyclopenta[g] [1]benzopyran-2-one was obtained as oil. The oil was crystallized from hexane (2.95 g, 96.7%). Recrystallization from ethanol-hexane gave colorless prisms, m.p. 154°–155° C.

Elemental analysis, for $C_{24}H_{25}NO_4$ Calcd.: C, 73.6 4; H, 6.44; N, 3.58 Found : C, 73.91; I{, 6.52; N, 3.60

6) To a solution of 3-tert-butyloxycarbonylamino-4-(2methylphenyl) -7,8-dihydro-6H-cyclopenta [g] [1]benzopyran-2-one (2.05 g) in dichloromethane (20 ml) was added trifluoroacetic acid (10 ml) dropwise with ice-cooling. The mixture was stirred under ice-cooling for 1 hour, after which the solvent was distilled off. The residue was diluted with water, neutralized with saturated aqueous solution of NaHCO$_3$ and extracted with chloroform. The extract was washed with water and dried (MgSO$_4$) and the solvent was distilled off to give crystals of 3-amino-4-(2-methylphenyl)-7,8-dihydro-6H-cyclopenta[g] [1]-benzopyran-2-one (1.5 g, 98.4%). Recrystallization from ethanol-dichloromethane gave colorless prisms, m.p. 275°–276° C.

Elemental analysis, for $C_{19}H_{17}NO_2$ Calcd.: C, 78.33; H, 5.88; N, 4.81 Found : C, 78.15; H, 5.85; N, 4.58

REFERENCE EXAMPLE 4

1) To a solution of 1-bromo-5,6,7,8-tetrahydro-2-naphthol (6.81 g) and triethylamine (4.2 ml) in dichloromethane (60 ml) was added 2-methylbenzoyl chloride (4.62 g) dropwise with ice-cooling. The mixture was stirred under ice cooling for 1 hour, after which it was washed with water and dried (MgSO$_4$). The solvent was then distilled off to give 1-bromo-2-(2-methylbenzoyloxy)-5,6,7,8-tetrahydronaphthalene as oil in quantitative yield.

2) A mixture of the 1-bromo-2-(2-methylbenzoyloxy) -5,6,7,8-tetrahydronaphthalene obtained in 1) and aluminum chloride (4.8 g) was heated at 120° C. for 1 hour. After cooling, the mixture was added to 2N HCl (50 ml)-ethyl acetate (50 ml). The ethyl acetate layer was taken, washed with water and dried (MgSO$_4$) and the solvent was distilled off, leaving an oil behind. To this oil was added ethanol to give crystals of 1-bromo -3-(2-methylbenzoyl)-5,6,7,8-tetrahydro-2-naphthol (4.0 g, 40.0%). Recrystallization from ethanol gave yellow prisms, m.p. 151°–153° C.

Elemental analysis, for $C_{18}H_{17}BrO_2$ Calcd.: C, 62.62; H, 4.96 Found: C, 62.52; H, 5.03

3) A mixture of 1-bromo-3-(2-methylbenzoyl)-5,6,7,8-tetrahydro-2-naphthol (3.33 g), sodium acetate (0.82 g), 5% palladium-on-carbon (50% hydrate, 1.0 g) and methanol (10 ml) was subjected to catalytic reduction. After the theoretical amount of hydrogen had been absorbed, the catalyst was filtered off. The solvent was then distilled off and the residue was diluted with water and extracted with ethyl acetate. The extract was washed with water and dried (MgSO$_4$) and the solvent was distilled off to give 3-(2-methylbenzoyl)-5,6,7,8-tetrahydro-2-naphthol as an oil (2.45 g, 96.5%).

4) A mixture of the 3-(2-methylbenzoyl)-5,6,7,8-tetrahydro-2-naphthol obtained in 3) (2.45 g), diethyl malonate (3.1 g) and DBU (0.14 ml) was heated at 170°–180° C. with stirring for 7 hours. After cooling, the reaction mixture was chromatographed on silica gel and eluted with hexane-ethyl acetate (85:15) to give ethyl 4-(2-methylphenyl)-2-oxo-6,7,8,9-tetrahydro-2H-naphtho[2,3-b]pyran-3-carboxylate as oil (3.0 g, 87.0%).

5) A mixture of the ethyl 4-(2-methylphenyl)-2-oxo-6,7,8,9-tetrahydro-2H-naphtho[2,3-b]pyran-3-carboxylate obtained in 4) (3.0 g), concentrated hydrochloric acid (10 ml) and acetic acid (10 ml) was refluxed for 17 hours. To this reaction mixture was added water to give crystals of 4-(2-methylphenyl)-2-oxo-6,7,8,9-tetrahydro-2H-naphtho[2,3-b]pyran-3-carboxylic acid (2.35 g, 84.8%). Recrystallization from acetone-hexane gave colorless prisms, m.p. 216°–217° C.

Elemental analysis, for $C_{21}H_{18}O_4$ Calcd.: C, 75.43; H, 5.43 Found : C, 75.33; H, 5.53

REFERENCE EXAMPLE 5

1) A mixture of 5-amino-6-(2-methylbenzoyl)indan (5.02 g), diethyl malonate (6.4 g) and DBU (0.3 ml) was heated at 170°–180° C. for 1 hour. To this reaction mixture was added ethanol to give crystals of ethyl 4-2-methylphenyl)-2-oxo-1,2,7,8-tetrahydro-6H -cyclopenta[g]quinoline-3-carboxylate (6.81 g, 98.1%). Recrystallization from ethanol-chloroform gave colorless crystals, m.p. 296°–298° C.

Elemental analysis, for $C_{22}H_{21}NO_3$ Calcd.: C, 76.06; H, 6.09; N, 4.03 Found : C, 76.11; It, 6.20; N, 4.18

2) To a mixture of ethyl 4-(2-methylphenyl)-2-oxo-1,2,7,8-tetrahydro-6H-cyclopenta[g]quinoline-3-carboxylate (3.0 g), potassium carbonate (1.43 g) and DMF (30 ml) was added methyl iodide (0.65 ml) dropwise. The mixture was stirred at room temperature for 10 hours, after which water was added to the reaction mixture to give crystals of ethyl 1-methyl-4-(2-methylphenyl)-2-oxo-1,2,7,8-tetrahydro-6H-cyclopenta[g]quinoline-3-carboxylate (2.95 g, 94.6%). Recrystallization from ethyl ether-isopropyl ether gave colorless needles, m.p. 134°–135° C.

Elemental analysis, for $C_{23}H_{23}NO_3$ Calcd.: C, 76.43; H, 6.41; N, 3.88 Found: C, 76.31; H, 6.60; N, 3.65

3) A mixture of ethyl 1-methyl-4-(2-methylphenyl)-2-oxo-1,2,7,8-tetrahydro-6H-cyclopenta[g]quinoline-3-carboxylate (2.0 g), potassium hydroxide (1.55 g) and 80% ethanol (20 ml) was stirred at 80° C. for 20 minutes. The mixture was diluted with water and acidified with 2N NCl to give crystals of 1-methyl-4-(2-methylphenyl)-2-oxo-1,2,7,8-tetrahydro-6H-cyclopenta[g]quinoline-3-carboxylic acid (1.85 g, 99.6%).

Recrystallization from acetone gave colorless prisms, m.p. 231°–232° C.

Elemental analysis, for $C_{21}H_{19}NO_3$ Calcd.: C, 75.66; H, 5.74; N, 4.20 Found: C, 75.78; H, 5.49; N, 4.00

REFERENCE EXAMPLE 6

1) The procedure of Reference Example 5°–1) was followed to synthesize ethyl 4-(2-chlorophenyl)-2-oxo-1,2,7,8-tetrahydro-6H-cyclopenta[g]quinoline-3-carboxylate. Yield 58.8%, mp. 285°–287° C. (recrystallized from ethanol-chloroform).

2) A mixture of the ethyl 4-(2-chlorophenyl)-2-oxo-1,2,7,8-tetrahydro-6H-cyclopenta[g]quinoline-3-carboxylate obtained in 1) (3.0 g) and phosphorus oxychloride (15 ml) was heated at 110° C. for 1 hour. The excess phosphorus oxychloride was distilled off and the residue was poured in water, neutralized with saturated aqueous solution of NaHCO$_3$ and extracted with ethyl acetate. The extract was washed with water, dried (MgSO$_4$) and distilled to remove the solvent. The procedure gave crystals of ethyl 2-chloro-4-(2-chlorophenyl)-7,8-dihydro-6H-cyclopenta[g]quinoline-3-carboxylate (2.85 g, 90.5%). Recrystallization from ethanol gave colorless needles.

Elemental analysis, for $C_{21}H_{17}Cl_2NO_2$ Calcd.: C, 65.20; H, 4.44; N, 3.63 Found : C, 65.12; H, 4.35; N, 3.65

3) To a solution of ethyl 2-chloro-4-(2-chlorophenyl)-7,8-dihydro-6H-cyclopenta[g]quinoline-3-carboxylate (1.93 g) in tetrahydrofuran-methanol (1:1, 15 ml) was added sodium methoxide (28% methanolic solution, 1.5 ml) dropwise. The mixture was stirred at room temperature for 3 hours, followed by addition of 2N NaOH (5 ml), and the mixture was heated at 80° C. for 30 minutes. The reaction mixture was diluted with water and adjusted to pH 4 with 2N HCl, whereupon crystals of 4-(2-chlorophenyl)-2-methoxy-6,7-dihydro-6H-cyclopenta [g]quinoline-3-carboxylic acid separated out (1.3 g, 73.4%). Recrystallization from methanol-chloroform gave colorless needles, m.p. 221°–222° C.

Elemental analysis, for $C_{20}H_{16}ClNO_3$ Calcd.: C, 67.90; H, 4.56; N, 3.86 Found: C, 67.80; H, 4.31; N, 3.93

REFERENCE EXAMPLE 7

1) To a mixture of 5-methoxyindan-6-carboxylic acid (3.84 g), DMF (0.1 ml) and tetrahydrofuran (50 ml) was added oxyalyl chloride (2.1 ml) dropwise. The mixture was stirred at room temperature for 1 hour, at the end of which time the solvent was distilled off to give 5-methoxyindan-6-carboxylic acid chloride. This chloride was dissolved in dichloromethane (50 ml) and after addition of 2,6-di-tert-butylphenol (4.12 g), tin tetrachloride (2.6 ml) was added dropwise with ice-cooling. The mixture was stirred under ice-cooling for 30 minutes and, then, poured in diluted hydrochloric acid. The organic layer was washed with water and dried (MgSO$_4$) and the solvent was distilled off. To the residue was added ethanol-hexane to give crystals of 5-(3,5-di-tert-butyl-4-hydroxybenzoyl)-6-methoxyindan (4.23 g, 55.7%). Recrystallization from ethanol gave colorless prisms, m.p. 154°–156° C.

Elemental analysis, for $C_{25}H_{32}O_3$ Calcd.: C, 78.91; H, 8.48 Found : C, 78.97; It, 8.62

2) To a solution of 5-(3,5-di-tert-butyl-4-hydroxybenzoyl)-6-methoxyindan (3.8 g) in dichloromethane (30 ml) was added boron tribromide-dichloromethane (1:2, 3 ml) dropwise with ice-cooling and stirring. The mixture was stirred under ice-cooling for 15 minutes, after which ethanol (5 ml) was added dropwise. The mixture was then washed with water and dried (MgSO$_4$) and the solvent was distilled off. To the residue was added hexane to give crystals of 5-(3,5-di -tert-butyl-4-hydroxybenzoyl)-6-hydroxyindan (3.06 g, 83.6% ) . Recrystallization from ethanol gave light yellow prisms, m.p. 155°–156° C.

Elemental analysis, for $C_{24}H_{30}O_3$ Calcd.: C, 78.65; H, 8.25 Found : C, 78.81; H, 8.20

3 ) A mixture of 5- ( 3,5-di-tert-butyl-4-hydroxybenzoyl)-6-hydroxyindan (2.8 g), diethyl malonate (3.6 g) and DBU (0.12 ml) was heated at 160°–170° C. for 2 hours. After cooling, the resulting crystals were collected by filtration and washed with ethanol to give ethyl 4-(3,5-di-tert-butyl-4-hydroxyphenyl)-2-oxo-2,6,7,8-tetrahydrocyclopenta [g] [1]benzopyran-3-carboxylate (3.1 g, 87.8%). Recrystallization from ethanol gave colorless prisms, m.p. 208°-209° C.

Elemental analysis, for $C_{29}H_{34}O_5$ Calcd.: C, 75.30; H, 7.41 Found : C, 75.19; H, 7.40

4) A mixture of ethyl 4-(3,5-di-tert-butyl-4-hydroxy -phenyl)-2-oxo-2,6,7,8-tetrahydrocyclopenta [g] [1]benzopyran-3-carboxylate (1.85 g), potassium hydroxide (1.12 g) and 80% ethanol (12 ml) was stirred at room temperature for 3 hours. The reaction mixture was then diluted with water, adjusted to pH4 with 6N HCl and extracted with ethyl acetate. The extract was washed with water and dried ($MgSO_4$) and the solvent was distilled off to give crystals of 4-3,5-di-tert-butyl-4-hydroxyphenyl)-2-oxo-2,6,7,8-tetrahydrocyclopenta[g] [1]benzopyran-3-carboxylic acid. The crystals were collected by filtration and washed with isopropyl ether (1.13 g, 64.9%). mp. 256°-260° C.

(g) Effects of the Invention

The compound (I) or a pharmaceutically acceptable salt thereof according to the present invention has excellent ACAT inhibitory activity and is of value as a medicine for the prevention and treatment of hypercholesterolemia and atherosclerosis or various associated diseases (viz. ischemic heart diseases such as myocardial infarction and cerebrovascular disorders such as cerebral infarction and cerebral apoplexy).

What we claim is:

1. A heterocyclic compound of the general formula:

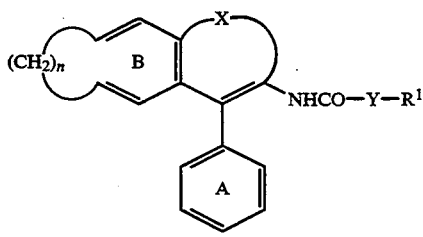

wherein ring A and ring B each mean a benzene ring which is unsubstituted or substituted by 1 to 4 substituents selected from a group consisting of a halogen, $C_{1-6}$ alkyl optionally halogenated, $C_{1-6}$ alkoxy optionally halogenated, $C_{1-6}$ alkylthio optionally halogenated, $C_{1-3}$ acyloxy, di-$C_{1-6}$ alkylamino and hydroxy; X means a group of the formula:

wherein $R^2$ is hydrogen, an alkyl or an alkoxy; m is 0 or 1, or the formula:

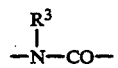

wherein $R^3$ is hydrogen or an alkyl; Y means a bond, —NH—, and $C_{1\,or\,2}$ alkylene group or —CH=CH—; $R^1$ is a $C_{1-8}$ alkyl, $C_{3-7}$ cycloalkyl, $C_{3-7}$ cycloalkyl-$C_{1-4}$ alkyl, $C_{6-10}$ aryl or $C_{7-16}$ aralkyl group optionally substituted by 1 to 5 substituents selected from a group consisting of a halogen, $C_{1-6}$ alkyl optionally halogenated, $C_{1-6}$ alkoxy optionally halogenated, $C_{1-6}$ alkylthio which may be halogenated, $C_{1-3}$ acyloxy, di-$C_{1-6}$ alkylamino and hydroxy; and n means a whole number of 3 through 6, or a pharmaceutically acceptable salt thereof.

2. A compound as claimed in claim 1, wherein the alkyl is a $C_{1-6}$ alkyl.

3. A compound as claimed in claim 1, wherein the alkoxy is a $C_{1-6}$ alkoxy.

4. A compound as claimed in claim 1, wherein the ring A is a benzene ring substituted by 1 to 3 substituents selected from a group consisting of halogen, $C_{1-6}$ alkyl and hydroxy; the ring B is a benzene ring; X is a group of the formula:

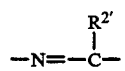

wherein $R^2$ is hydrogen or a $C_{1-6}$ alkoxy, the formula:

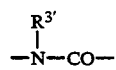

wherein $R^3$ is a $C_{1-6}$ alkyl; Y is —NH—, an $C_{1\,or\,2}$ alkylene group or —CH=CH—; $R^1$ is a phenyl group substituted by 1 to 3 substituents selected from a group consisting of a halogen, $C_{1-6}$ alkyl, $C_{1-6}$ alkoxy, $C_{1-6}$ acyloxy, di-$C_{1-6}$ alkylamino and hydroxy; and n is 3.

5. A compound as claimed in claim 1, wherein the ring A is a benzene ring substituted by halogen or $C_{1-6}$ alkyl; the ring B is a benzene ring; X is a group of the formula: —N=CH—; Y is —NH—; $R^1$ is

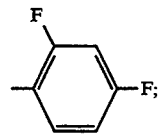

and n is 3

6. A compound as claimed in claim 5, which is N-[4-(2-chlorophenyl)-7,8-dihydro-6H-cyclopenta[g]quinolin -3-yl]-N'-(2,4-difluorophenyl)urea.

7. An acyl-CoA:cholesterol acyltransferase inhibitor composition which contains an effective amount of a heterocyclic compound of the general formula:

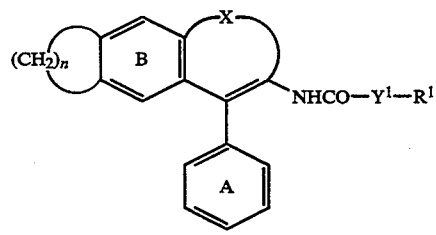

wherein ring A and ring B each means a benzene ring which is unsubstituted or substituted by 1 to 4 substituents selected from a group consisting of a halogen, $C_{1-6}$ alkyl optionally halogenated, $C_{1-6}$ alkoxy optionally halogenated, $C_{1-6}$ alkylthio optionally halogenated, $C_{1-3}$ acyloxy, di-$C_{1-6}$ alkylamino and hydroxy, X means a group of the formula:

wherein $R^2$ is hydrogen, an alkyl or an alkoxy; m is 0 or 1, or the formula:

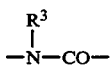

wherein $R^3$ is hydrogen or an alkyl; Y means a bond, —NH—, an $C_{1 \text{ or } 2}$ alkylene or —CH=CH—; $R^1$ is a $C_{1-8}$ alkyl, $C_{3-7}$ cycloalkyl, $C_{3-7}$ cycloalkyl-$C_{1-4}$ alkyl, $C_{6-10}$ aryl or $C_{7-16}$ aralkyl group which may be substituted by 1 to 5 substituents selected from a group consisting of a halogen, $C_{1-6}$ alkyl optionally halogenated, $C_{1-6}$ alkoxy optionally halogenated, $C_{1-6}$ alkylthio optionally halogenated, $C_{1-3}$ acyloxy, di-$C_{1-6}$ alkylamino and hydroxy; and n means a whole number of 3 through 6, or a pharmaceutically acceptable salt thereof, optionally together with a pharmaceutically acceptable carrier.

8. A method for inhibiting acyl-CoA:cholesterol acyltransferase which comprises administrating an effective amount of a compound as claimed in claim 1 optionally together with a pharmaceutically acceptable carrier to a mammal requiring such inhibition.

* * * * *

UNITED STATES PATENT AND TRADEMARK OFFICE
CERTIFICATE OF CORRECTION

PATENT NO. : 5,418,239   Page 1 of 4
DATED : May 23, 1995
INVENTOR(S) : MEGURO et al.

It is certified that error appears in the above-indentified patent and that said Letters Patent is hereby corrected as shown below:

Cover page, item [57], the compound should appear as shown below:

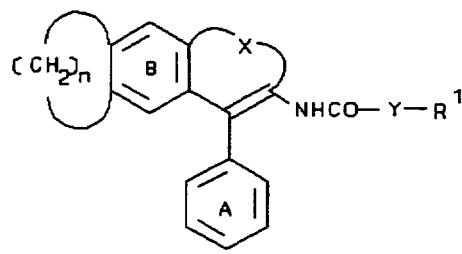

Column 2, line 20, compound IV should appear as shown below:

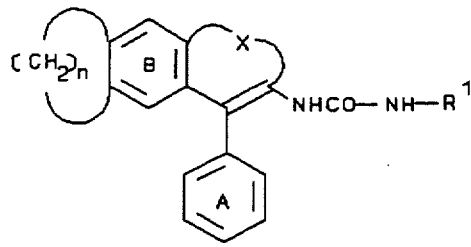

UNITED STATES PATENT AND TRADEMARK OFFICE
CERTIFICATE OF CORRECTION

PATENT NO. : 5,418,239  Page 2 of 4
DATED     : May 23, 1995
INVENTOR(S) : MEGURO et al.

It is certified that error appears in the above-indentified patent and that said Letters Patent is hereby corrected as shown below:

line 34, compound II should appear as shown below:

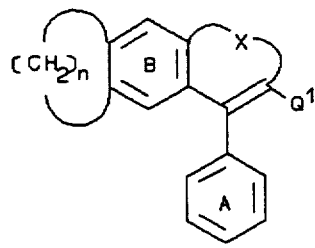

line 55, compound VII should appear as shown below:

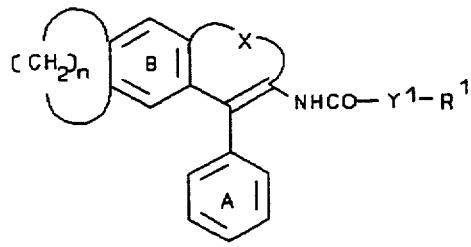

UNITED STATES PATENT AND TRADEMARK OFFICE
CERTIFICATE OF CORRECTION

PATENT NO. : 5,418,239
DATED : May 23, 1995
INVENTOR(S) : MEGURO et al.

It is certified that error appears in the above-indentified patent and that said Letters Patent is hereby corrected as shown below:

Column 6, line 20, compound VIII should appear as shown below:

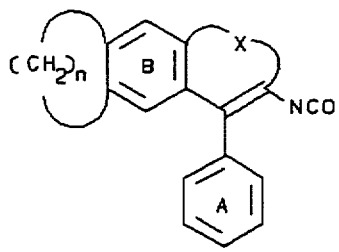

line 41, compound V should appear as shown below:

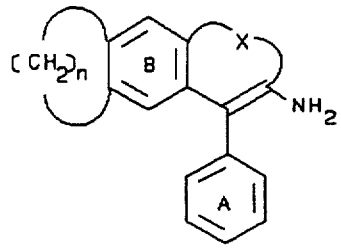

UNITED STATES PATENT AND TRADEMARK OFFICE
CERTIFICATE OF CORRECTION

PATENT NO. : 5,418,239
DATED : May 23, 1995
INVENTOR(S) : MEGURO et al.

It is certified that error appears in the above-indentified patent and that said Letters Patent is hereby corrected as shown below:

Column 33, line 34, Claim 1, the compound should appear as shown below:

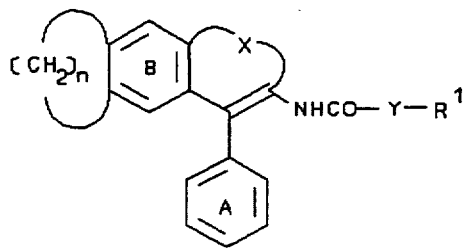

Signed and Sealed this

Ninth Day of January, 1996

Attest:

BRUCE LEHMAN

Attesting Officer

Commissioner of Patents and Trademarks